(12) United States Patent
Miller et al.

(10) Patent No.: US 9,724,362 B2
(45) Date of Patent: *Aug. 8, 2017

(54) PHARMACEUTICAL COMPOSITIONS COMPRISING NANOPARTICLES AND A RESUSPENDING MATERIAL

(75) Inventors: Warren Kenyon Miller, Bend, OR (US); Daniel Smithey, Bend, OR (US); Benjamin Lee Frankamp, Rockaway Beach, OR (US); Ralph Tadday, Bend, OR (US)

(73) Assignee: Bend Research, Inc., Bend, OR (US)

( * ) Notice: Subject to any disclaimer, the term of this patent is extended or adjusted under 35 U.S.C. 154(b) by 226 days.

This patent is subject to a terminal disclaimer.

(21) Appl. No.: 12/746,754

(22) PCT Filed: Dec. 5, 2008

(86) PCT No.: PCT/US2008/013433
§ 371 (c)(1),
(2), (4) Date: Jul. 30, 2010

(87) PCT Pub. No.: WO2009/073215
PCT Pub. Date: Jun. 11, 2009

(65) Prior Publication Data
US 2010/0310663 A1 Dec. 9, 2010

Related U.S. Application Data

(60) Provisional application No. 60/992,790, filed on Dec. 6, 2007.

(51) Int. Cl.
*A61K 31/74* (2006.01)
*A61K 47/38* (2006.01)
(Continued)

(52) U.S. Cl.
CPC ............ *A61K 31/74* (2013.01); *A61K 9/1652* (2013.01); *A61K 9/5161* (2013.01); *A61K 9/5192* (2013.01); *A61K 47/38* (2013.01)

(58) Field of Classification Search
CPC ...... A61K 31/74; A61K 47/38; A61K 9/1652; A61K 9/5161; A61K 9/5192
See application file for complete search history.

(56) References Cited

U.S. PATENT DOCUMENTS

| 3,960,757 A | 6/1976 | Morishita et al. |
| 4,107,288 A | 8/1978 | Oppenheim et al. |

(Continued)

FOREIGN PATENT DOCUMENTS

| EP | 877033 A1 | 11/1998 |
| EP | 1180062 B1 | 3/2004 |

(Continued)

OTHER PUBLICATIONS

Al-Kassas, R., "Design and In Vitro Evaluation of Gentamicin-Eudragit Microspheres Intended for Intra-Ocular Administration," Journal of Microencapsulation, 21:1(2004)71-81.

(Continued)

*Primary Examiner* — Aradhana Sasan
(74) *Attorney, Agent, or Firm* — Klarquist Sparkman, LLP

(57) ABSTRACT

A pharmaceutical composition comprises nanoparticles comprising a poorly water-soluble drug and a poorly aqueous soluble polymer, and a resuspending material selected from the group consisting of hydroxypropyl methyl cellulose acetate succinate, carboxymethyl ethylcellulose, and pharmaceutically acceptable salt forms thereof.

19 Claims, 1 Drawing Sheet

(51) Int. Cl.
*A61K 9/51* (2006.01)
*A61K 9/16* (2006.01)

(56) References Cited

U.S. PATENT DOCUMENTS

| | | |
|---|---|---|
| 4,158,707 A | 6/1979 | Steffen |
| 4,229,360 A | 10/1980 | Schneider |
| 4,298,594 A | 11/1981 | Sears |
| 4,329,332 A | 5/1982 | Couvreur et al. |
| 4,331,654 A | 5/1982 | Morris |
| 4,501,726 A | 2/1985 | Schroder |
| 4,610,868 A | 9/1986 | Fountain et al. |
| 4,615,881 A | 10/1986 | Deibig et al. |
| 4,639,370 A | 1/1987 | Carli |
| 4,649,155 A | 3/1987 | Steffen |
| 4,725,442 A | 2/1988 | Haynes |
| 4,728,513 A | 3/1988 | Ventouras |
| 4,731,210 A | 3/1988 | Weder et al. |
| 4,754,027 A | 6/1988 | Applegren |
| 4,826,689 A | 5/1989 | Violanto |
| 4,830,858 A | 5/1989 | Payne |
| 4,837,381 A | 6/1989 | Steber et al. |
| 4,857,336 A * | 8/1989 | Khanna et al. ............... 424/473 |
| 4,880,634 A | 11/1989 | Speiser |
| 4,882,164 A | 11/1989 | Ferro et al. |
| 4,904,479 A | 2/1990 | Illum |
| 4,917,900 A | 4/1990 | Jones et al. |
| 4,997,454 A | 3/1991 | Violante |
| 5,049,322 A | 9/1991 | Devissaguet et al. |
| 5,051,261 A | 9/1991 | McGinity |
| 5,084,278 A | 1/1992 | Mehta |
| 5,085,864 A | 2/1992 | Cannon et al. |
| 5,091,187 A | 2/1992 | Haynes |
| 5,091,188 A | 2/1992 | Haynes |
| 5,112,621 A | 5/1992 | Stevens et al. |
| 5,118,528 A | 6/1992 | Fessi et al. |
| 5,133,908 A | 7/1992 | Stainmesse et al. |
| 5,145,684 A | 9/1992 | Liversidge et al. |
| 5,152,923 A | 10/1992 | Weder |
| 5,174,930 A | 12/1992 | Stainmesse et al. |
| 5,188,837 A | 2/1993 | Domb |
| 5,202,159 A | 4/1993 | Chen et al. |
| 5,298,262 A | 3/1994 | Na |
| 5,302,401 A | 4/1994 | Liversidge et al. |
| 5,314,506 A | 5/1994 | Midler et al. |
| 5,336,507 A | 8/1994 | Na |
| 5,340,591 A | 8/1994 | Nakano et al. |
| 5,352,459 A | 10/1994 | Hollister et al. |
| 5,370,880 A | 12/1994 | Jones et al. |
| 5,445,830 A | 8/1995 | Ishizue et al. |
| 5,456,923 A | 10/1995 | Nakamichi et al. |
| 5,470,583 A | 11/1995 | Na |
| 5,484,608 A | 1/1996 | Rudnic et al. |
| 5,494,683 A | 2/1996 | Liversidge et al. |
| 5,508,276 A * | 4/1996 | Anderson et al. ............ 514/183 |
| 5,510,118 A | 4/1996 | Bosch et al. |
| 5,534,270 A | 7/1996 | De Castro |
| 5,543,158 A | 8/1996 | Gref et al. |
| 5,552,160 A | 9/1996 | Liversidge et al. |
| 5,556,642 A | 9/1996 | Kobayashi et al. |
| 5,560,931 A | 10/1996 | Eickhoff et al. |
| 5,560,932 A | 10/1996 | Bagchi et al. |
| 5,565,188 A | 10/1996 | Wong et al. |
| 5,565,215 A | 10/1996 | Gref et al. |
| 5,569,448 A | 10/1996 | Wong et al. |
| 5,569,469 A | 10/1996 | Lovrecich |
| 5,571,536 A | 11/1996 | Eickhoff et al. |
| 5,573,783 A | 11/1996 | Desieno |
| 5,576,016 A | 11/1996 | Amselem |
| 5,578,325 A | 11/1996 | Domb et al. |
| 5,585,108 A | 12/1996 | Ruddy et al. |
| 5,622,938 A | 4/1997 | Wong |
| 5,662,883 A | 9/1997 | Bagchi et al. |
| 5,662,932 A | 9/1997 | Amselem |
| 5,665,277 A | 9/1997 | Johnson et al. |
| 5,665,331 A | 9/1997 | Bagchi et al. |
| 5,667,800 A | 9/1997 | De Vringer |
| 5,679,690 A | 10/1997 | Andre et al. |
| 5,683,723 A | 11/1997 | Spenlehauer et al. |
| 5,705,196 A | 1/1998 | Galan Valdivia et al. |
| 5,707,634 A | 1/1998 | Schmitt |
| 5,716,642 A | 2/1998 | Bagchi et al. |
| 5,718,919 A | 2/1998 | Ruddy |
| 5,780,062 A | 7/1998 | Frank et al. |
| 5,783,211 A | 7/1998 | Manzo et al. |
| 5,785,976 A | 7/1998 | Westesen |
| 5,834,025 A | 11/1998 | de Garavilla et al. |
| 5,843,509 A | 12/1998 | Calvo Salve et al. |
| 5,853,753 A | 12/1998 | Maierhofer et al. |
| 5,874,111 A | 2/1999 | Maitra et al. |
| 5,885,486 A | 3/1999 | Westesen |
| 5,889,051 A | 3/1999 | Chen et al. |
| 5,919,408 A | 7/1999 | Muller et al. |
| 5,932,249 A | 8/1999 | Gruber et al. |
| 5,935,939 A | 8/1999 | Kararli et al. |
| 5,952,005 A | 9/1999 | Olsson et al. |
| 5,962,566 A * | 10/1999 | Grandfils ............ A61K 9/5153 424/499 |
| 5,968,551 A | 10/1999 | Oshlack |
| 6,007,845 A | 12/1999 | Domb et al. |
| 6,020,004 A | 2/2000 | Shah |
| 6,027,747 A | 2/2000 | Terracol |
| 6,083,529 A | 7/2000 | Manzo et al. |
| 6,139,870 A | 10/2000 | Verrecchia |
| 6,143,211 A | 11/2000 | Mathiowitz et al. |
| 6,146,663 A | 11/2000 | Bissery et al. |
| 6,153,225 A | 11/2000 | Lee |
| 6,177,103 B1 | 1/2001 | Pace et al. |
| 6,197,348 B1 | 3/2001 | Morella et al. |
| 6,197,349 B1 | 3/2001 | Westesen |
| 6,207,178 B1 | 3/2001 | Westesen |
| 6,217,901 B1 | 4/2001 | Perrott |
| 6,235,224 B1 | 5/2001 | Mathiowitz et al. |
| 6,245,349 B1 | 6/2001 | Yiv et al. |
| 6,254,889 B1 | 7/2001 | Kigoshi et al. |
| 6,267,985 B1 | 7/2001 | Chen |
| 6,267,989 B1 | 7/2001 | Liversidge et al. |
| 6,268,053 B1 | 7/2001 | Woiszwillo et al. |
| 6,270,806 B1 | 8/2001 | Liversidge |
| 6,280,770 B1 | 8/2001 | Pather et al. |
| 6,303,560 B1 | 10/2001 | Hartan et al. |
| 6,361,944 B1 | 3/2002 | Mirkin et al. |
| 6,375,986 B1 | 4/2002 | Ryde |
| 6,383,500 B1 | 5/2002 | Wooley et al. |
| 6,391,338 B1 | 5/2002 | Frisbee et al. |
| 6,406,745 B1 | 6/2002 | Talton |
| 6,428,814 B1 | 8/2002 | Bosch et al. |
| 6,440,458 B1 | 8/2002 | Yamashita et al. |
| 6,443,898 B1 | 9/2002 | Unger et al. |
| 6,447,806 B1 | 9/2002 | Gassmann |
| 6,458,383 B2 | 10/2002 | Chen et al. |
| 6,462,093 B1 | 10/2002 | Miyamoto |
| 6,479,146 B1 | 11/2002 | Caruso et al. |
| 6,485,743 B1 | 11/2002 | Jung et al. |
| 6,509,034 B1 | 1/2003 | Calanchi et al. |
| 6,517,859 B1 | 2/2003 | Tice et al. |
| 6,537,579 B1 | 3/2003 | Desai et al. |
| 6,544,497 B2 | 4/2003 | Zhu et al. |
| 6,548,264 B1 | 4/2003 | Tan et al. |
| 6,551,619 B1 | 4/2003 | Penkler et al. |
| 6,555,139 B2 | 4/2003 | Sharma |
| 6,565,873 B1 | 5/2003 | Shefer |
| 6,565,875 B2 | 5/2003 | Tice et al. |
| 6,565,885 B1 | 5/2003 | Tarara et al. |
| 6,576,264 B1 | 6/2003 | Henriksen et al. |
| 6,579,519 B2 | 6/2003 | Maitra et al. |
| 6,592,899 B2 | 7/2003 | Fowers et al. |
| 6,592,901 B2 | 7/2003 | Durig et al. |
| 6,592,903 B2 | 7/2003 | Ryde |
| 6,596,262 B2 | 7/2003 | Zhu et al. |
| 6,596,311 B1 | 7/2003 | Dobetti |
| 6,607,784 B2 | 8/2003 | Kipp et al. |
| 6,616,869 B2 | 9/2003 | Mathiowitz et al. |
| 6,620,351 B2 | 9/2003 | Gupta |

(56) References Cited

U.S. PATENT DOCUMENTS

| | | | |
|---|---|---|---|
| 6,623,761 B2 | 9/2003 | Hassan | |
| 6,632,671 B2 | 10/2003 | Unger | |
| 6,638,537 B2 | 10/2003 | Dennis et al. | |
| 6,638,621 B2 | 10/2003 | Anderson | |
| 6,638,994 B2 | 10/2003 | Crooks et al. | |
| 6,645,517 B2 | 11/2003 | West et al. | |
| 6,645,569 B2 | 11/2003 | Cramer et al. | |
| 6,649,192 B2 | 11/2003 | Alonso Fernandez et al. | |
| 6,652,967 B2 | 11/2003 | Yadav et al. | |
| 6,656,504 B1 | 12/2003 | Bosch et al. | |
| 6,656,507 B2 | 12/2003 | Petereit et al. | |
| 6,656,984 B1 | 12/2003 | Haasmaa et al. | |
| 6,660,382 B2 | 12/2003 | Nouri et al. | |
| 6,663,885 B1 | 12/2003 | Hager et al. | |
| 6,669,959 B1 | 12/2003 | Adjei et al. | |
| 6,677,386 B1 | 1/2004 | Giezen et al. | |
| 6,682,761 B2 | 1/2004 | Pace | |
| 6,682,895 B2 | 1/2004 | Mirkin et al. | |
| 6,685,960 B1 | 2/2004 | Gasco | |
| 6,692,769 B1 | 2/2004 | Ishibashi et al. | |
| 6,696,084 B2 | 2/2004 | Pace et al. | |
| 6,709,622 B2 | 3/2004 | Billiet | |
| 6,720,008 B2 | 4/2004 | Allison | |
| 6,726,934 B1 | 4/2004 | Prokop | |
| 6,746,635 B2 | 6/2004 | Mathiowitz et al. | |
| 6,755,915 B1 | 6/2004 | Van Soest et al. | |
| 6,756,062 B2 | 6/2004 | Johnston et al. | |
| 6,761,903 B2 | 7/2004 | Chen et al. | |
| 6,780,324 B2 | 8/2004 | Le Garrec et al. | |
| 6,793,938 B2 | 9/2004 | Sankaram | |
| 6,824,791 B2 | 11/2004 | Mathiowitz et al. | |
| 6,827,946 B2 | 12/2004 | Hirsh | |
| 6,863,914 B1 | 3/2005 | Auweter et al. | |
| 6,869,617 B2 | 3/2005 | Kipp et al. | |
| 6,878,693 B2 | 4/2005 | Goldshtein | |
| 6,887,493 B2 | 5/2005 | Shefer | |
| 6,890,512 B2 | 5/2005 | Roser et al. | |
| 7,081,450 B2 | 7/2006 | Goldshtein | |
| 7,105,176 B2 | 9/2006 | Auweter et al. | |
| 2002/0012675 A1 | 1/2002 | Jain et al. | |
| 2002/0054914 A1 | 5/2002 | Morcol | |
| 2002/0068092 A1 | 6/2002 | Bosch et al. | |
| 2002/0081334 A1 | 6/2002 | Johnston et al. | |
| 2002/0106403 A1 | 8/2002 | Parikh et al. | |
| 2002/0127278 A1 | 9/2002 | Kipp et al. | |
| 2002/0142017 A1 | 10/2002 | Simonnet | |
| 2003/0003155 A1 | 1/2003 | Kipp et al. | |
| 2003/0026844 A1 | 2/2003 | Lee et al. | |
| 2003/0031719 A1 | 2/2003 | Kipp et al. | |
| 2003/0049323 A1 | 3/2003 | Hitt et al. | |
| 2003/0095928 A1 | 5/2003 | McGurk et al. | |
| 2003/0129239 A1 | 7/2003 | Goldshtein | |
| 2003/0147965 A1 | 8/2003 | Bassett et al. | |
| 2003/0166509 A1 | 9/2003 | Edwards et al. | |
| 2003/0170309 A1 | 9/2003 | Babcock et al. | |
| 2003/0190347 A1 | 10/2003 | Supersaxo et al. | |
| 2003/0206949 A1 | 11/2003 | Parikh et al. | |
| 2003/0235619 A1 | 12/2003 | Allen et al. | |
| 2004/0009229 A1 | 1/2004 | Unger et al. | |
| 2004/0013613 A1 | 1/2004 | Jain et al. | |
| 2004/0018229 A1 | 1/2004 | Henriksen et al. | |
| 2004/0018236 A1 | 1/2004 | Gurny et al. | |
| 2004/0047913 A1 | 3/2004 | Allemann et al. | |
| 2004/0067251 A1 | 4/2004 | Johnston et al. | |
| 2004/0071776 A1 | 4/2004 | Boudy et al. | |
| 2004/0091546 A1 | 5/2004 | Johnson | |
| 2004/0180005 A1 | 9/2004 | Jurgens | |
| 2004/0191319 A1 | 9/2004 | Yun | |
| 2004/0220081 A1 | 11/2004 | Kreitz et al. | |
| 2004/0245662 A1 | 12/2004 | Chaubal et al. | |
| 2004/0247624 A1 | 12/2004 | Unger et al. | |
| 2005/0013866 A1 | 1/2005 | Maincent et al. | |
| 2005/0238716 A1 | 10/2005 | Verrijk et al. | |
| 2006/0134220 A1 | 6/2006 | Aboubakar et al. | |
| 2006/0159766 A1* | 7/2006 | Jenkins | A61K 9/127 424/489 |
| 2007/0190129 A1* | 8/2007 | Ahmed et al. | 424/451 |
| 2007/0287719 A1* | 12/2007 | Boyden et al. | 514/265.1 |
| 2009/0028948 A1* | 1/2009 | Payne | A61K 9/5123 424/489 |
| 2010/0215747 A1* | 8/2010 | Bloom et al. | 424/487 |
| 2010/0233272 A1* | 9/2010 | Appel | A61K 9/146 424/489 |
| 2010/0266692 A1* | 10/2010 | Bloom et al. | 424/488 |

FOREIGN PATENT DOCUMENTS

| | | |
|---|---|---|
| EP | 710261 B1 | 5/2004 |
| WO | WO 9710811 A1 | 3/1997 |
| WO | WO 9713503 A1 | 4/1997 |
| WO | WO 9933558 A1 | 7/1999 |

OTHER PUBLICATIONS

Amrite, A.C., S.P. Ayalasomayajula, and U. Kompella, "Ocular Distribution of Intact Nano- and Micro Particles Following Subconjunctival and Systemic Routes of Administration," Drug Delivery Techn., vol. 2, No. 3, 2003.

Barbu, E., L. Verestiuc, T.G. Nevell, and J. Tsibouldis, "Polymeric Materials for Ophthalmic Drug Delivery: Trends and Perspectives," J. of Materials Chemistry, 16(2006)3439-3443.

Bodmeier et al., "Preparation and Evaluation of Drug-Containing Polymeric Nanosuspensions," presented at the 5th International Conference on Pharmaceutical Technology, Paris, France, 1989. Proceedings vol. 2, pp. 265-268.

Bodmeier, et al., "Indomethacin Polymer Nanosuspension Prepared by Microfluidization", Journal of Controlled Release, 12 (1990) 223-233.

Bourges, J.-L., S.E. Gautier, F. Delie, R.A. Bejjani, J.-C. Jeanny, R. Gurny, D. BenEzra, and F.F. Behar-Cohen, "Ocular Drug Delivery Targeting the Regina and Retinal Pigment Epithelium Using Polylactide Nanoparticles," Investigative Ophthalmology and Visual Science, 44:8(2003)3562-3569.

Briancon, S., H. fessi, F. Lecomet, and J. Lieto, "Study and Scale-Up of a Nanoprecipitation Process," Industrial Crystallization 1999 (IChemE), pp. 1-10.

Bucolo, C., A. Maltese, F. Maugeri, B. Busa, G. Puglisi, and R. Pignatello, "Eudragit RL100 Nanoparticle System for the Ophthalmic Delivery of Cloricromene," Journal of Pharmacy and Pharmacology, 56(2004)841 846.

Calvo, P., J.L. Vila-Jato, and M.J. Alonso, "Evaluation of Cationic Polymer-Coated Nanocapsules as Ocular Drug Carriers," International Journal of Pharmaceutics, 153(1997)41-50.

Carrasquillo, K.G., J.A. Ricker, I.K. Rigas, J.W. Miller, E.S. Gragoudas, and A.P. Adamis, "Controlled Delivery of the Anti-VEGF Aptamer EYE001 with Poly(lactic-co-glycolic) Acid Microspheres," Investigative Ophthalmology and Visual Science, 44:1(2003)290-299.

Cavalli, R., M.R. Gasco, P. Chetoni, S. Burgalassi, and M.F. Saettone, "Solid Lipid Nanoparticles (SLN) as Ocular Delivery System for Tobramycin," International J. Pharmaceutics, 238(2002)241-245.

Chen et al., "Comparison of Albumin and Casein Microspheres as a Carrier for Doxorubicin," J. Pharm. Pharmacol.39(1987)978-985.

Chiou, W.L., and S.Riegelman, J. Pharm. Sci., 60:9(1971)1281-1302.

Couvreur, Microspheres and Drug Therapy, Elsevier, (1984) pp. 103-115.

De, T.K., D.J. Rodman, B.A. Holm, P.N. Prasad, and E.J. Bergey, "Brimonidine Formulation in Polyacrylic Acid Nanoparticles for Ophthalmic Delivery," J. Microencapsualtion, 20:3)2003)361-374.

Decampos, A.M., A. Sanchez, and M.J. Alonso, "Chitosan Nanoparticles: A New Vehicle for the Improvement of the Delivery of Drugs to the Ocular Surface. Application to Cyclosporin A," International J. of Pharmaceutics, 224(2001)159-168.

Decampos., A.M., A. Sanchez, R. Gref, P. Calvo, and M.J. Alonso, "The Effect of a PGE Versus a Chitosan Coating on the Interaction

(56) References Cited

OTHER PUBLICATIONS of Drug Colloidal Carriers with the Ocular Mucosa," European Journal of Pharmaceutical Sciences, 20(2003)73-81.
Dejaeghere, F., E. Allemann, J.-C. Leroux, W. Stevels, J. Feijen, E. Doelker, and R. Gurny, "Formulation of Lyoprotection of Poly(Lactic Acid-Co-Ethylene Oxide) Nanoparticles: Influence on Physical Stability and in Vitro cell Uptake," Pharmaceutical Research, 16:6(1999)859-866.
Desai, S.D., and J. Blanchard, "Pluronic F127-Based Ocular Delivery System Containing Biodegradable Polyisobutylcyanoacrylate Nanocapsules of Pilocarpine," Drug Delivery, 7(2000)201-207.
Fee, C.A., and R.I. Pettigrew, "National Institute of Biomedical Imaging and Bioengineering: Poised for the Future," National Institute of Biomedical Imaging and Bioengineering, 229:3(2003)636-637.
Fessi, H., F. Puisieux, J.Ph. Devissaguet, N. Ammoury, and S. Benita, "Nanocapsule Formation by Interfacial Polymer Deposition Following Solvent Displacement," International J. of Pharmaceutics, 55(1989)R1-R4.
Ford, J.L., Pharm. Acta Helv., 61:3(1986)69-87.
Fox et al., from Proteins in Food Processing, R.Y. Yada (ed), CRC Press, 2004, Chapter 3: The Caseins pp. 29-71.
Gavini, E., P. Chetoni, M. Cossu, M.G. Alvarez, M.F. Saettone, and P. Giunchedi, "PLGA Microspheres for the Ocular Delivery of a Peptide Drug, Vancomycin Using Emulsification/Spray-Drying as the Preparation Method: In Vitro/In Vivo Studies," European Journal of Pharmaceutics and Biopharmaceutics, 57(2004)207-212.
Giannavola, C., C. Bucolo, A. Maltese, D. Paolino, M.A. Vandelli, G. Puglisi, V.H.L. Lee, and M. Fresta, "Influence of Preparation Conditions on Acyclovir-Loaded Poly-d,l-Lactic Acid Nanospheres and Effect of PEG Coating on Ocular Drug Bioavailability." Pharmaceutical Research, 20:4(2003)584-590.
Gurny, Drug Develop. Ind. Pharm. 7(1), 1-25, 1981.
Gurny, R., T. Boye, and H. Ibrahim, "Ocular Therapy with Nanoparticulate Systems for Controlled Drug Delivery," Journal of Controlled Release, 2(1985)353-361.
Harmia, J. Microencapsulation, 1986 vol. 3, No. 1, p. 3-12.
Hasegawa, H., et al., Chem. Pharm. Bull., 33:4(1985)1615-1619; Chem. Pharm. Bull., 34:5(1986)2183-2190; Chem. Pharm. Bull., 36:12(1988) 4941-4950.
Herrero-Vanrell, R., and M.F. Refojo, "Biodegradable Microspheres for Vitreoretinal Drug Delivery," Advanced Drug Delivery Reviews, 52(2001)5 16.
Hornig et al., "Novel Nanoparticles Based on Dextran Esters with Unsaturated Moieties," Macromolecular Rapid Commun., 2005, 26, 1908-1912.
Hornig et al., "Structure Design of Multifunctional Furoate and Pyroglutamate Esters of Dextran by Polymer-Analogous Reactions," Macromol. Biosci. 2007, 7, 297-306.
Hsiue, G.-H., S.-H. Hsu, C.-C. Yang, S.-H. Lee,a nd I.-K. Yang, "Preparation of Controlled Release Ophthalmic Drops, for Glaucoma Therapy Using Thermosensitive poly-N-Isopropylacrylamide," Biomaterials, 23(2002)457 462.
Kim, S., Y.T. Lim, E.G. Soltesz, A.M. DeGrand, J. Lee, A. Nakayama, J.A. Parker, T. Mihaljevic, R.G. Laurence, D.M. Dor, L.H. Cohn, M.G. Bawendi, and J.V. Frangioni,"Near-Infrared Fluorescent Type II Quantum Dots for Sentinel Lymph Node Mapping," Nature Biotechnology, 22:1(2004)93-97.
Knepp et al., Synthesis, Properties, and Intratumoral Evaluation of Mitoxantrone-Loaded Casein Microspheres in Lewis Lung Carcinoma, J. Pharm. Pharmacol., 45(1993)887-891.
Kompella, U.B., N. Bandi, and S.P. Ayalasomayajula, "Subconjunctival Nano- and Microparticles Sustain Retinal Delivery of Budesonide, a Corticosteroid Capable of Inhibiting VEGF Expression," Investigative Ophthalmology and Visual Science, 44:3(2003)1192-1201.
Kumar, M.N.V., "Nano and Microparticles as Controlled Drug Delivery devices," J. Pharm. Pharmaceutical Sciences, 3:2(2000)234-258.

Latha et al., Casein as a Carrier Matrix for 5-Fluorouracil: Drug Release from Microspheres, Drug-Protein Conjugates and In-Vivo Degradation of Microspheres in Rat Muscle, J. Pharm. Pharmacol., 46(1994)858-862.
Latha et al., Glutaraldehyde Cross-Linked Bovine Casein Microspheres as a Matrix for the Controlled Release of Theophylline: In Vitro Studies, J. Pharm. Pharmacol., 46(1994)8-13.
Latha et al., Progesterone Release from Glutaraldehyde Cross-Linked Casein Microspheres: In Vitro Studies and In Vivo Response in Rabbits, Contraception, 61(2000)329-334.
Lecorre, P., J.H. Rytting, V. Gajan, F. Chevanne, and R. LeVerge, "In Vitro Controlled Release Kinetics of Local Anaesthetics from Poly(D,L-lactice) and Poly (lactice-co-glycolide) Microspheres," Journal of Microencapsulation, 1997, pp. 243-255.
Lellemand, F., O. Felt-Baeyens, K. Besseghir, F. Behar-Cohen, and R. Gurny, "Cyclosporine A Delivery to the Eye: A Pharmaceutical Challenge," European J. of Pharmaceutics and Biopharmaceutics, 56(2003)307 318.
Lemarchand, C., R. Gref, and P. Couvreur, "Polysaccharide-Decorated Nanoparticles," European J. of Pharmaceutics and Biopharmaceutics, 580,327-341, 2004.
Lemarchand, et al., "Influence of polysaccharide coating on the interactions of nanoparticles with biological systems," Biomaterials, 27(2006)108-118.
Liebert, et al., "Nanoparticles on the Basis of Highly Functionalized Dextrans," J. Am. Chem. Soc. 2005, 127, 10484-10485.
Longmuir, K.J., R.T. Robertson, S.M. Haynes, J.L. Baratta, and A.J. Waring, "Effective Targeting of Liposomes to Liver and Hepatocytes In Vivo by Incorporation of a Plasmodium Amino Acid Sequence," Pharmaceutical Research, 23:4(2006)759-769.
Losa, C., L. Marchal-Heussler, F. Orallo, J.L. Vila Jato, and M.J. Alonso, "Design of New Formulations for Topical Ocular Administration: Polymeric Nanocapsules Containing Metipranolol," Pharmaceutical Research, 10:1(1993)80-87.
Merodio, M., J.M. Irache, F. Valamanesch, and M. Mirshahi, "Ocular Disposition and Tolerance of Ganciclovir-Loaded Albumin Nanoparticles after Intravitreal Injection in Rats," Biomaterials, 23(2002)1587-1594.
Mirshahi et al., Development of Drug Delivery Systems from Vegetal Proteins: Legumin Nanoparticles, Drug Dev. Indust.Pharm., 22:8(1996)841-846.
Mora-Gutierrez et al., Modeling Calcium-Induced Solubility in Caprine Milk Caseins Using a Thermodynamic Linkage Approach, J. Dairy Sci., 76(1993)3698-3710.
Ohio State FST 822 Class Lecture, Casein, 2006, 5 pp.
Pignatello, R., C. Bucolo, and G. Puglisi, "Ocular Tolerability of Eudragit RS100 and RL100 Nanosuspensions as Carriers for Ophthalmic Controlled Drug Delivery," Journal of Pharmaceutical Sciences, 91:12(2002)2636-2641.
Pignatello, R., C. Bucolo, G. Spedalieri, A. Maltese, and G. Puglisi, "Flurbiprofen-Loaded Acrylate Polymer Nanosuspensions for Ophthalmic Application," Biomaterials, 23(2002)3247-3255.
Pignatello, R., C. Bucolo, P. Ferra, A. Maltese, A. Puleo, and G. Puglisi, "Eudragit RS100 Nanosuspensions for the Ophthalmic Controlled Delivery of Ibuprofen," European Journal of Pharmaceutical Sciences, 16(2002)53 61.
Qaddoumi, M.G., H. Ueda, J. Yang, J. Davda, V. Labhasetwar, and V.H.L. Lee, "The Characteristics and Mechanisms of Uptake of PLGA Nanoparticles in Rabbit Conjuctival Epithelial Cell Layers," Pharmaceutical Research, 21:4(2004)641-648.
Raveendran, P., J. Fu, and S.L. Wallen, "Completely 'Green' Synthesis and Stabilization of Metal Nanoparticles," J. American Chemical Society, 125(2003)13940-13941.
Santinho et al., Influence of Formulation on the Physiochemical Properties of Casein Microparticles, Int'l J. Pharm., 186(1999)191-198.
Scholes, P.D., A.G.A. Coombes, L. Illum, S.S. Savis, M. Vert, and M.C. Davies, "The Preparation of Sub-200 nm Poly(lactide-co-glycolide) Microspheres for Site-Specific Drug Delivery," J. Controlled Release, 25(1993)145-153.
Sjostrom, et al., Journal of Pharmaceutical Sciences, vol. 82, No. 6 Jun. 1993, pp. 584-589.

(56) References Cited

OTHER PUBLICATIONS

Sugimoto, I., K. Sasaki, A. Kuchiki, T. Ishihara, and H. Nakagawa, Chem. Pharm. Bull, 30:12(1982)4479-4488.

Suverkrup, R., S. Grunthal, O. Krasichkova, S. Maier, A. Weischselbaum, B. Neff, M. Diestelhorst, S. Dinslage, and A. Lux, "The Ophthalmic Lyophilisate Carrier System (OLCS): Development of a Novel Dosage Form, Freeze-Drying Technique, and In Vitro Quality Control Tests, "European J. Pharmaceutics and Biopharmaceutics, 57(2004)269-277.

Takayama, K., N. Nambu, and T. Nagai., Chem. Pharm. Bull., 30:2(1982)673-678.

Takenaka, H., Y. Kawashima and S.Y. Lin, J. Pharm. Sci., 69:12(1980)1388-1392.

Takeuchi, H., T. Handa and Y. Kawashima, Chem. Pharm. Bull., 35:9(1987)3800-3806.

Tuovinen, L., E. Ruhanen, T. Kinnarinen, S. Ronkko, J. Pelkonen, A. Urtti, S. Peltonen, and K. Jarvinen, "Starch Acetate Microparticles for Drug Delivery Into Retinal Pigment Epithelium—In Vitro Study," J. of Controlled Release, 98(2004)407-413.

Ueda, M., A. Iwara, and J. Kreuter, "Influence of the Preparation Methods on the Drug Release Behaviour of Loperamide-Loaded Nanoparticles," J. Microencapsulation, 15:3(1998)361-372.

University of Guelph, Dairy Chemistry and Physics, 2006, 16 pp.

Vandamme, Th.F., "Microemulsions as Ocular Drug Delivery Systems: Recent Developments and Future Challenges," Progress in Retinal and Eye Research, 21(2002)15-34.

Vandervoort, J., and A. Ludwig, "Preparation and Evaluation of Drug-Loaded Gelatin Nanoparticles for Topical Ophthalmic Use," European J. of Pharmaceutics and Biopharmaceutics, 57(2004)251-261.

Willmott et al., Doxorubicin-Loaded Casein Microspheres: Protean Nature of Drug Incorporation J. Pharm. Pharmacol. 42(1992)472-475.

Zahr, A.S., M. de Villiers, and M.V. Pishko, "Encapsulation of Drug Nanoparticles in Self-Assembled Macromolecular Nanoshells," Langmuir, 21(2005)503 410.

Zimmer, A., and J. Kreuter, "Microspheres and Nanoparticles Used in Ocular Delivery Systems," Advanced Drug Delivery Reviews, 16(1995)61-73.

\* cited by examiner

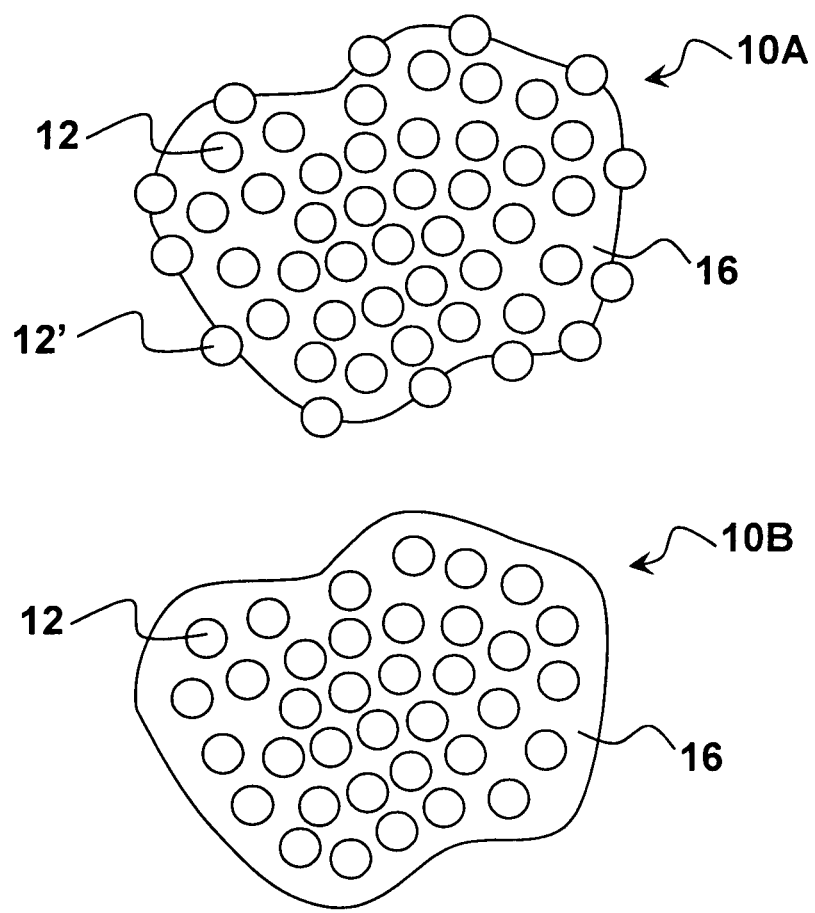

PHARMACEUTICAL COMPOSITIONS COMPRISING NANOPARTICLES AND A RESUSPENDING MATERIAL

This is a 371 of PCT/US2008/013433 filed Dec. 5, 2008, and claims priority of U.S. 60/992,790 filed Dec. 6, 2007.

BACKGROUND OF THE INVENTION

The present invention relates to compositions comprising nanoparticles comprising a low-solubility drug and a poorly aqueous soluble polymer, and a resuspending material selected from the group consisting of hydroxypropyl methylcellulose acetate succinate (HPMCAS), carboxymethyl ethylcellulose (CMEC), and pharmaceutically acceptable salt forms thereof.

It is known that poorly water-soluble drugs may be formulated as nanoparticles. Nanoparticles are of interest for a variety of reasons, such as to improve the bioavailability of poorly water-soluble drugs, to provide targeted drug delivery to specific areas of the body, to reduce side effects, or to reduce variability in vivo.

A variety of approaches have been taken to formulate drugs as nanoparticles. One approach is to decrease the size of crystalline drug by grinding or milling the drug in the presence of a surface modifier. See, e.g., U.S. Pat. No. 5,145,684. Another approach to forming nanoparticles is to precipitate the drug in the presence of a film forming material such as a polymer. See, e.g., U.S. Pat. No. 5,118,528.

There remain a number of problems associated with the use of nanoparticles to deliver pharmaceutical compounds to the body. The nanoparticles must be stabilized so that they do not aggregate into larger particles in aqueous suspensions. Often surface modifiers such as surfactants are used to stabilize the nanoparticles, but such materials can have adverse physiological effects when administered in vivo. In addition, without a surface modifier present, the surface of the nanoparticles is unprotected, leading to a decrease in performance and stability.

In addition, it is often desirable to formulate nanoparticles as a dry material to improve patient compliance and facilitate incorporating the nanoparticles into a suitable dosage form. However, when liquids are removed from suspensions of nanoparticles, the nanoparticles often agglomerate or aggregate. When the resulting dry material is then administered to an aqueous solution (either in vitro or in vivo), large particles are formed, corresponding to the agglomerated or aggregated nanoparticles. These aggregates or agglomerated particles reduce the performance of the formulation.

Accordingly, there is still a continuing need for nanoparticles that are stable, in the sense of not forming crystalline drug over time or aggregating into larger particles, and that improve the bioavailability of low-solubility drugs.

BRIEF SUMMARY OF THE INVENTION

In one aspect, a solid pharmaceutical composition comprises:
(a) nanoparticles comprising a poorly water soluble drug and a poorly aqueous soluble polymer, wherein (i) the poorly water soluble drug has a solubility in water of less than 5 mg/mL over the pH range of 6.5 to 7.5; (ii) at least 90 wt % of the drug in the nanoparticles is in a non-crystalline form; and (iii) the nanoparticles have an average size of less than 500 nm; and (b) a resuspending material selected from the group consisting of hydroxypropyl methyl cellulose acetate succinate (HPMCAS), carboxymethyl ethylcellulose (CMEC), and pharmaceutically acceptable salt forms thereof; wherein the resuspending material constitutes from 5 wt % to 90 wt % of the combined mass of (1) said resuspending material and (2) said nanoparticles.

The compositions provide a number of advantages over the prior art. Because the pharmaceutical composition comprises (a) nanoparticles comprising a poorly water soluble drug and a polymer, and (b) a resuspending material selected from the group consisting of HPMCAS, CMEC, and pharmaceutically acceptable salt forms thereof, the stability of the non-crystalline drug in the nanoparticles and the stability of nanoparticle suspensions can be addressed independently, resulting in nanoparticles with improved performance and stability.

HPMCAS and CMEC when used as resuspending materials prevent agglomeration of the nanoparticles into larger particles in aqueous suspensions and readily form a nanoparticle suspension after administration of the dry, solid pharmaceutical compositions to an aqueous environment. Both HPMCAS and CMEC are enteric polymers. HPMCAS was originally developed as an enteric polymer for pharmaceutical dosage forms and for providing halation-preventing layers on photographic films. See Onda et al., U.S. Pat. No. 4,226,981. CMEC was developed as an enteric polymer for pharmaceutical dosage forms. Enteric polymers are those that remain intact in the acidic environment of the stomach; dosage forms coated with such polymers protect the drug from the acidic environment or prevent irritation of the stomach by the drug.

In contrast to their conventional use as an enteric coating or otherwise as an enteric material to provide sustained release of the drug, both HPMCAS and CMEC are used in the present pharmaceutical compositions as a resuspending material to rapidly produce nanoparticles when the dry, solid composition is administered to a neutral pH, aqueous environment, and to reduce the rate of agglomeration of the nanoparticles when suspended in an aqueous environment. The use of HPMCAS or CMEC as the resuspending material has the advantage that after nanoparticles are formed, the nanoparticles retain their size during processing, so that they may be formulated into dry, solid compositions. In addition, upon administration of the dry, solid pharmaceutical compositions to an aqueous environment, such as the gastrointestinal tract, the resuspending material rapidly dissolves in a neutral pH environment to release nanoparticles, and reduces agglomeration of the nanoparticles.

The poorly aqueous soluble polymer used to form the nanoparticles may be selected to stabilize the poorly aqueous soluble drug in the nanoparticle. The polymer is therefore chosen to be poorly aqueous soluble so that a portion of the poorly aqueous soluble drug is soluble in the polymer. This prevents or reduces the rate of crystallization of the non-crystalline drug in the nanoparticle. It is well known that the non-crystalline form of a low-solubility drug provides a greater aqueous concentration of drug relative to the crystalline form of the drug when administered to an aqueous use environment. However, it is also well known that when the drug is not stabilized in the non-crystalline form, the drug rapidly converts to the crystalline form in the use environment. See, for example, Hancock and Parks (Pharmaceutical Research, Vol. 17, No. 4, 2000). Thus, a poorly aqueous soluble polymer is selected to maintain the stability of the non-crystalline drug in the nanoparticle, resulting in an enhanced concentration of free drug when the nanoparticle is administered to an aqueous use environment.

Accordingly, the combination of a resuspending material selected from HPMCAS, CMEC, and pharmaceutically acceptable salt forms thereof, with nanoparticles comprising a poorly aqueous soluble polymer, results in solid compositions that provide a nanoparticle suspension when administered to an aqueous solution. Such compositions provide improved bioavailability of the drug when administered in vivo.

The foregoing and other objectives, features, and advantages of the invention will be more readily understood upon consideration of the following detailed description of the invention.

BRIEF DESCRIPTION OF THE SEVERAL VIEWS OF THE DRAWINGS

FIG. 1. shows schematically a solid composition of the present invention.

DETAILED DESCRIPTION OF THE INVENTION

Compositions are provided comprising (a) a plurality of nanoparticles comprising the drug and the poorly aqueous soluble polymer, and (b) a resuspending material selected from the group HPMCAS, CMEC, and pharmaceutically acceptable salt forms thereof. Pharmaceutical compositions, nanoparticles, polymers, drugs, optional surface stabilizers, and methods for making nanoparticles and the compositions are described in detail below.

Solid Pharmaceutical Compositions

In one aspect, a dry, solid pharmaceutical composition comprises (a) a plurality of nanoparticles comprising a poorly water-soluble drug and a poorly aqueous soluble polymer, and (b) a resuspending material selected from HPMCAS, CMEC, or pharmaceutically acceptable salt forms thereof. As used herein, the term "dry, solid pharmaceutical composition" means that the composition is in a solid form and substantially free of liquids.

The solid pharmaceutical composition may take one of many configurations. In one embodiment, at least a portion of the nanoparticles in the solid composition are encapsulated by the resuspending material. By "at least a portion of the nanoparticles are encapsulated by the resuspending material" means that the resuspending material encapsulates at least a portion of the plurality of nanoparticles in the composition. The resuspending material may encapsulate only a portion of nanoparticles, or may encapsulate essentially all of the nanoparticles in the composition. Preferably, the resuspending material encapsulates essentially all of the nanoparticles in the composition.

For example, FIG. 1 shows schematically a composition 10A comprising nanoparticles 12 encapsulated by the resuspending material 16. Those nanoparticles 12' not encapsulated by the resuspending material 16 have at least a portion of their surfaces in contact with the resuspending material 16. Composition 10B has essentially all of the nanoparticles 12 encapsulated with the resuspending material 16. Thus, the compositions may contain a plurality of nanoparticles, at least a portion of which are encapsulated by the resuspending material; those nanoparticles not encapsulated by the resuspending material are in direct contact with the resuspending material.

In another embodiment, a portion of the resuspending material is adsorbed to the surface portion of the nanoparticles. The remaining portion of the resuspending material encapsulates the nanoparticles in the composition. In this embodiment, the resuspending material may act as a surface stabilizer, stabilizing the nanoparticles during the formation process or when present in aqueous suspension, reducing or preventing aggregation or flocculation of the nanoparticles prior to forming the solid composition of the invention.

The resuspending material is selected from HPMCAS, CMEC, or pharmaceutically acceptable salt forms thereof. By "pharmaceutically acceptable salt forms thereof" is meant the HPMCAS or CMEC is in a pharmaceutically acceptable salt form, or that the composition was formulated with HPMCAS or CMEC in the presence of a counterion when the dry, solid pharmaceutical composition was formed. Exemplary counterions suitable for forming salt forms include sodium, potassium, ammonium, calcium, magnesium, aluminum, iron, and amines. Preferably, the HPMCAS or CMEC is in a sodium salt form, potassium salt form, or ammonium salt form.

HPMCAS is currently commercially available from Shin-Etsu Chemical (Tokyo, Japan), known by the trade name "AQOAT." Shin-Etsu manufactures three grades of AQOAT that have different combinations of substituent levels to provide enteric protection at various pH levels. The AS-LF and AS-LG grades (the "F" standing for fine and the "G" standing for granular) provide enteric protection up to a pH of about 5.5. The AS-MF and AS-MG grades provide enteric protection up to a pH of about 6.0, while the AS-HF and AS-HG grades provide enteric protection up to a pH of about 6.8. Shin Etsu gives the following specifications for these three grades of AQOAT polymers:

| Substituent | Composition of Shin Etsu's AQOAT Polymers (wt %) | | |
| --- | --- | --- | --- |
| | L Grades | M Grades | H Grades |
| Methoxyl Content | 20.0-24.0 | 21.0-25.0 | 22.0-26.0 |
| Hydroxypropoxyl Content | 5.0-9.0 | 5.0-9.0 | 6.0-10.0 |
| Acetyl Content | 5.0-9.0 | 7.0-11.0 | 10.0-14.0 |
| Succinoyl | 14.0-18.0 | 10.0-14.0 | 4.0-8.0 |

A preferred grade of HPMCAS is the L grade, having a methoxyl content of from 20 to 24 wt %, a hydroxypropoxyl content of from 5 to 9 wt %, an acetyl content of from 5 to 9 wt %, and a succinoyl content of from 14 to 18 wt %.

An exemplary grade of CMEC is the product manufactured by Freund Corporation (Tokyo, Japan).

Salt forms of HPMCAS and CMEC are preferred because the salt forms of these resuspending materials rapidly dissolve in a neutral pH aqueous environment, thereby producing a nanoparticle suspension when the dry, solid composition is administered to an aqueous solution. In one embodiment, the resuspending material is a salt form of HPMCAS. In a preferred embodiment, the salt counterion is selected from the group consisting of sodium, potassium and ammonium.

In another embodiment, the resuspending material is a salt form of CMEC. In a preferred embodiment, the salt counterion is selected from the group consisting of sodium, potassium and ammonium.

The resuspending material constitutes from 5 wt % to 90 wt % of the combined mass of (1) the resuspending material and (2) the nanoparticles. The resuspending material is preferably present in a sufficient amount so that a solid composition forms a nanoparticle suspension when administered to an aqueous use environment. Furthermore, preferably a sufficient amount of resuspending material is present to prevent or retard agglomeration of the nanoparticles into larger particles following administration to an aqueous use environment. In one embodiment, the resuspending material constitutes from 10 wt % to 75 wt % of the combined mass of (1) the resuspending material and (2) the nanoparticles. In another embodiment, the resuspending material constitutes from 15 wt % to 50 wt % of the combined mass of (1) the resuspending material and (2) the nanoparticles. In still another embodiment, the resuspending material constitutes at least 10 wt % of the combined mass of (1) the resuspending material and (2) the nanoparticles. In still another embodiment, the resuspending material constitutes at least 20 wt % of the combined mass of (1) the resuspending material and (2) the nanoparticles. In yet another embodiment, the resuspending material constitutes at least 25 wt % of the combined mass of (1) the resuspending material and (2) the nanoparticles. In another embodiment, the resuspending material constitutes at least 40 wt % of the combined mass of (1) the resuspending material and (2) the nanoparticles. In another embodiment, the resuspending material constitutes at least 50 wt % of the combined mass of (1) the resuspending material and (2) the nanoparticles.

Nanoparticles

The nanoparticles comprise the drug and the poorly aqueous soluble polymer. By "nanoparticles" is meant a plurality of small particles in which the average size of the particles in suspension is less than about 500 nm. In suspension, by "average size" is meant the effective cumulant diameter as measured by dynamic light scattering, using for example, Brookhaven Instruments' 90Plus particle sizing instrument. By "size" is meant the diameter for spherical particles, or the maximum diameter for non-spherical particles. Preferably, the average size of the nanoparticles is less than 400 nm, more preferably less 300 nm, most preferably less than 200 nm.

The width of the particle size distribution in suspension is given by the "polydispersity" of the particles, which is defined as the relative variance in the correlation decay rate distribution, as is known by one skilled in the art. See B. J. Fisken, "Revisiting the method of cumulants for the analysis of dynamic light-scattering data," Applied Optics, 40(24), 4087-4091 (2001) for a discussion of cumulant diameter and polydispersity. Preferably, the polydispersity of the nanoparticles is less than 0.5. More preferably, the polydispersity of the nanoparticles is less than about 0.3. In one embodiment, the average size of the nanoparticles is less than 500 nm with a polydispersity of 0.5 or less. In another embodiment, the average size of the nanoparticles is less than 300 nm with a polydispersity of 0.5 or less. In still another embodiment, the average size of the nanoparticles is less than 200 nm with a polydispersity of 0.5 or less. In yet another embodiment, the average size of the nanoparticles is less than 200 nm with a polydispersity of 0.3 or less.

While the drug in its pure form may be either crystalline or non-crystalline, at least 90 wt % of the drug in the nanoparticles is non-crystalline. The term "crystalline," as used herein, means a particular solid form of a compound that exhibits long-range order in three dimensions. "Non-crystalline" refers to material that does not have long-range three-dimensional order, and is intended to include not only material which has essentially no order, but also material which may have some small degree of order, but the order is in less than three dimensions and/or is only over short distances. Another term for a non-crystalline form of a material is the "amorphous" form of the material. As previously discussed, the non-crystalline form of a low-solubility drug is preferred as it provides a greater aqueous concentration of drug relative to the crystalline form of the drug in an aqueous use environment. Preferably at least about 95 wt % of the drug in the nanoparticle is non-crystalline; in other words, the amount of drug in crystalline form does not exceed about 5 wt %. Amounts of crystalline drug may be measured by Powder X-Ray Diffraction (PXRD), by Differential Scanning Calorimetry (DSC), by solid state nuclear magnetic resonance (NMR), or by any other known quantitative measurement.

The non-crystalline drug in the nanoparticle can exist as a pure phase, as a solid solution of drug homogeneously distributed throughout the polymer, or any combination of these states or those states that lie between them. In one embodiment, at least a portion of the drug and the polymer is present in the nanoparticle in the form of a solid solution. The solid solution may be thermodynamically stable, in which the drug is present at less than the solubility limit of the drug in the polymer, or may be a supersaturated solid solution in which the drug exceeds its solubility limit in the polymer. In another embodiment, essentially all of the drug and the polymer is present as a solid solution.

The nanoparticles can exist in a number of different configurations. In one embodiment, the nanoparticles comprise a core, the core comprising the non-crystalline drug and the poorly aqueous soluble polymer. As used herein, the term "core" refers to the interior portion of the nanoparticle. The nanoparticles also have a "surface portion," meaning the outside or exterior portion of the nanoparticle. Thus, the nanoparticles consist of a core (i.e., the interior portion) and a surface portion. In some embodiments, described herein below, materials may be adsorbed to the surface portion of the nanoparticle. Materials adsorbed to the surface portion of the nanoparticle are considered part of the nanoparticle, but are distinguishable from the core of the nanoparticle. Methods to distinguish materials present in the core versus materials adsorbed to the surface portion of the nanoparticle include (1) thermal methods, such as differential scanning calorimetry (DSC); (2) spectroscopic methods, such as X-ray photoelectron spectroscopy (XPS), transmission electron microscopy (TEM) with energy dispersive X-ray (EDX) analysis, Fourier transform infra red (FTIR) analysis, and Raman spectroscopy; (3) chromatographic techniques, such as high performance liquid chromatography (HPLC), and gel-permeation chromatography (GPC); and (4) other techniques known in the art.

In one embodiment, the non-crystalline drug and the poorly aqueous soluble polymer together constitute at least 60 wt % of the core, more preferably at least 80 wt % of the core. In another embodiment, the core consists essentially of the non-crystalline drug and the poorly aqueous soluble polymer.

The non-crystalline drug present in the core can exist in non-crystalline pure drug domains, as a thermodynamically stable solid solution of non-crystalline drug homogeneously distributed throughout the polymer, as a supersaturated solid solution of non-crystalline drug homogeneously distributed throughout the polymer, or any combination of these states or those states that lie between them. When the glass-transition temperature ($T_g$) of the non-crystalline drug is different from the $T_g$ of the pure polymer by at least about 20° C., the core may exhibit a $T_g$ that is different from the $T_g$ of pure non-crystalline drug or pure polymer.

In still another embodiment, the core comprises the non-crystalline drug and the poorly aqueous soluble polymer, with the resuspending material adsorbed to the surface portion of the nanoparticle.

The mass ratio of drug to polymer in the nanoparticle can range from about 1:999 to about 9:1 (that is, from about 0.1 wt % drug to 90 wt % drug relative to the total mass of drug and polymer in the nanoparticle). Preferably, the mass ratio of drug to polymer ranges from about 1:99 to about 4:1 (that is, from about 1 wt % to about 80 wt % drug relative to the total mass of drug and polymer), more preferably from about 1:19 to about 3:1 (that is, from about 5 wt % to about 75 wt %), even more preferably from about 1:9 to about 2:1 (that is, from about 10 wt % to about 67 wt % drug relative to the total mass of drug and polymer in the nanoparticle), and most preferably from about 1:3 to about 3:2 (that is, from about 25 wt % to about 60 wt % drug relative to the total mass of drug and polymer in the nanoparticle). In one embodiment, the mass ratio of drug to polymer is less than 9:1, preferably less than 4:1, more preferably less than 3:1, and most preferably less than 3:2. In another embodiment, the mass ratio of drug to polymer is at least 1:999, preferably at least 1:99, more preferably at least 1:9, and most preferably at least 1:3.

To minimize the total mass of the formulation, high drug loadings are desired. However, if the amount of drug in the nanoparticle is too high, the nanoparticle suspension becomes unstable, resulting in crystallization of the drug in the suspension. Additionally, high amounts of drug in the nanoparticle can lead to crystalline drug formation when the nanoparticles are isolated from suspension in solid form. In absolute terms, it is generally preferred that the amount of drug in the nanoparticle be less than about 90 wt %, more preferably less than about 80 wt %, even more preferably less than about 75 wt % the total mass of the nanoparticle.

Preferred embodiments of nanoparticles have the following amounts of drug and poorly aqueous soluble polymer:

10 to 75 wt %, preferably 20 to 50 wt % drug; and
20 to 75 wt %, preferably 25 to 70 wt % poorly aqueous soluble polymer.

Poorly Aqueous Soluble Polymers

The term "polymer" is used conventionally, meaning a compound that is made of monomers connected together to form a larger molecule. A polymer generally consists of at least about 20 monomers connected together. Thus, the molecular weight of the polymer generally will be about 2000 daltons or more. The polymer should be inert, in the sense that it does not chemically react with the drug in an adverse manner, and should be pharmaceutically acceptable.

The polymer is poorly aqueous soluble. By "poorly aqueous soluble" is meant that the polymer has a solubility of less than 0.1 mg/mL when administered alone at a concentration of 0.2 mg/mL to PBS at pH 6.5. A test to determine the aqueous solubility of a polymer may be performed as follows. The polymer is initially present in bulk powder form with average particle sizes of greater than about 1 micron. The polymer alone is administered at a concentration of 0.2 mg/ml to the pH 6.5 PBS and stirred for approximately 1 hour at room temperature. Next, a nylon 0.45 μm filter is weighed, and the polymer solution is filtered. The filter is dried overnight at 40° C., and weighed the following morning. The amount of polymer dissolved (e.g., the solubility of the polymer) is calculated from the amount of polymer added to the pH 6.5 PBS minus the amount of polymer remaining on the filter (mg). The polymer is considered to be poorly aqueous soluble if it has a solubility of less than 0.1 mg/mL in this test. Preferably, when administered at a concentration of 0.2 mg/mL to the pH 6.5 PBS, a poorly aqueous soluble polymer has a solubility of less than 0.07 mg/mL, more preferably less than 0.05 mg/mL, and most preferably less than 0.01 mg/mL.

It is preferred that the polymer be soluble in an organic solvent. Preferably the polymer has a solubility in an organic solvent of at least about 0.1 mg/mL, and preferably at least 1 mg/mL. Preferably the polymer is not crosslinked.

In one embodiment, the polymer is non-ionizable, meaning that the polymer possesses substantially no ionizable functional groups. By "substantially no ionizable functional groups" is meant that the number of ionizable groups covalently attached to the polymer is less than about 0.05 milliequivalents per gram of polymer. Preferably, the number is less than about 0.02 milliequivalents per gram of non-ionizable polymer. By "ionizable groups" is meant functional groups that are at least about 10% ionized over at least a portion of the physiologically relevant pH range of 1 to 8. Such groups have $pK_a$ values of about 0 to 9.

Suitable polymers include substituted cellulosics, and non-cellulosics. By "cellulosic" is meant a cellulose polymer that has been modified by reaction of at least a portion of the hydroxyl groups on the cellulose repeating units with a compound to form an ester or an ether substituent.

In order to be poorly aqueous soluble, the polymer must be hydrophobic, meaning that the polymer has a sufficient number of hydrophobic groups relative to hydrophilic groups. In a preferred embodiment, the poorly aqueous soluble cellulosic polymer has an ether- or ester-linked alkyl substituent. Suitable alkyl substituents include $C_1$ to $C_4$ alkyl groups. Exemplary ether-linked substituents include methyl, ethyl, propyl, and butyl groups. Exemplary ester-linked substituents include acetate, propionate, and butyrate groups.

Exemplary poorly aqueous soluble substituted cellulosics include ethylcellulose, propylcellulose, butylcellulose, cellulose acetate, cellulose propionate, cellulose butyrate, cellulose acetate propionate, cellulose acetate butyrate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, and hydroxypropyl methylcellulose butyrate. Preferably, the poorly aqueous soluble polymer is selected from the group consisting of ethylcellulose, cellulose acetate, cellulose propionate, cellulose butyrate, cellulose acetate butyrate.

Exemplary non-cellulosics include vinyl polymers and copolymers, such as poly(vinyl acetate), poly(vinyl acetate-co-vinyl alcohol), and poly(ethylene-co-vinyl acetate); polymethacrylate and polyacrylate polymers and copolymers, such as poly(ethyl acrylate-co-methyl methacrylate), available as EUDRAGIT® NE; polylactones, such as poly(lactide), poly(glycolide), poly(ε-caprolactone), and copolymers of these, including poly(lactide-co-glycolide), poly(lactide-co-ε-caprolactone), poly(ethylene oxide-co-ε-caprolactone), poly(ethylene oxide-co-lactide), and poly(ethylene oxide-co-lactide-co-glycolide); and poly(alkyl) cyanoacrylates, such as poly(isobutyl)cyanoacrylate, and poly(hexyl)cyanoacrylate; and mixtures thereof.

In one embodiment, the poorly aqueous soluble polymer is selected from the group consisting of ethylcellulose, propylcellulose, butylcellulose, cellulose acetate, cellulose propionate, cellulose butyrate, cellulose acetate propionate, cellulose acetate butyrate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, hydroxypropyl methylcellulose butyrate, poly(vinyl acetate), poly(vinyl acetate-co-vinyl alcohol), poly(ethylene-co-vinyl acetate), poly(ethyl acrylate-co-methyl methacrylate), poly(lactide), poly(glycolide), poly(ε-caprolactone), poly(lactide-co-glycolide), poly(lactide-co-ε-caprolactone), poly(ethylene oxide-co-ε-caprolactone), poly(ethylene oxide-co-lactide), poly(ethylene oxide-co-lactide-co-glycolide, poly(isobutyl)cyanoacrylate, and poly(hexyl)cyanoacrylate.

In another embodiment, the poorly aqueous soluble polymer is selected from the group consisting of ethylcellulose, propylcellulose, butylcellulose, cellulose acetate, cellulose propionate, cellulose butyrate, cellulose acetate propionate, cellulose acetate butyrate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, and hydroxypropyl methylcellulose butyrate.

In another embodiment, the poorly aqueous soluble polymer is selected from the group consisting of ethylcellulose, cellulose acetate, cellulose propionate, cellulose butyrate, and cellulose acetate butyrate. In still another embodiment, the poorly aqueous soluble polymer is ethylcellulose.

Surface Stabilizers

The nanoparticles of the present invention may optionally comprise a surface stabilizer in addition to the drug and the polymer. The purpose of the surface stabilizer is to reduce or prevent aggregation or flocculation of the nanoparticles in an aqueous suspension, resulting in nanoparticles with improved stability. In one embodiment, the surface stabilizer is used to stabilize the nanoparticles during the formation process. The stabilizer should be inert, in the sense that it does not chemically react with the drug in an adverse manner, and should be pharmaceutically acceptable.

When a surface stabilizer is present, it may constitute from 0.1 wt % to about 40 wt % of the total mass of the nanoparticles. Generally, lower concentrations of surface stabilizer are preferred. Thus, preferably the surface stabilizer constitutes about 35 wt % or less, more preferably about 30 wt % or less, and most preferably about 25 wt % or less the total mass of the nanoparticles.

In one embodiment, the poorly water soluble drug, the polymer, the optional surface stabilizer, and the resuspending material constitute at least 90 wt % of the solid composition of the invention. In another embodiment, the solid composition of the invention consists essentially of the poorly water soluble drug, the polymer, the optional surface stabilizer, and the resuspending material.

In one embodiment, the surface stabilizer is an amphiphilic compound, meaning that it has both hydrophobic and hydrophilic regions. In another embodiment, the surface stabilizer is a surfactant, including anionic, cationic, zwitterionic, and non-ionic surfactants. Mixtures of surface stabilizers may also be used.

Exemplary surface stabilizers include casein, caseinates, polyvinyl pyrrolidone (PVP), polyoxyethylene alkyl ethers, polyoxyethylene stearates, polyoxyethylene castor oil derivatives, poly(ethylene oxide-propylene oxide) (also known as poloxamers), tragacanth, gelatin, polyethylene glycol, bile salts (such as salts of dihydroxy cholic acids, including sodium and potassium salts of cholic acid, glycocholic acid, and taurocholic acid), phospholipids (such as phosphatidyl cholines, including 1,2-diacylphosphatidylcholine also referred to as PPC or lecithin), sodium dodecylsulfate (also known as sodium lauryl sulfate), benzalkonium chloride, sorbitan esters, polyoxyethylene alkyl ethers, polyoxyethylene castor oil derivatives, polyoxyethylene sorbitan fatty acid esters (polysorbates), polyoxyethylene stearates, triethanolamine, sodium docusate, sodium stearyl fumarate, sodium cyclamate, and mixtures and pharmaceutically acceptable forms thereof.

In one embodiment the surface stabilizer is an ionizable surface stabilizer selected from the group consisting of sodium and potassium salts of cholic acid, glycocholic acid, and taurocholic acid.

Preferred embodiments of nanoparticles have the following amounts of drug, poorly aqueous soluble polymer, and optional surface stabilizer:

10 to 75 wt %, preferably 20 to 50 wt % drug;

20 to 75 wt %, preferably 25 to 70 wt % poorly aqueous soluble polymer; and 0.1 to 40 wt %, preferably 1 to 30 wt % optional surface stabilizer.

The Drug

The drug is a "poorly water soluble drug," meaning that the drug has a solubility in water (over the pH range of 6.5 to 7.5 at 25° C.) of less than 5 mg/mL. The utility of the invention increases as the water solubility of the drug decreases. The drug may have an even lower solubility in water, such as less than about 1 mg/mL, less than about 0.1 mg/mL, and even less than about 0.01 mg/mL.

In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (i.e., solutions with pH 1-8), including USP simulated gastric and intestinal buffers, and dose is in mg. Thus, a dose-to-aqueous solubility ratio may be calculated by dividing the dose (in mg) by the aqueous solubility (in mg/mL).

Preferred classes of drugs include, but are not limited to, compounds for use in the following therapeutic areas: antihypertensives, antianxiety agents, antiarrythmia agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, triglyceride-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-angiogenesis agents, anti-glaucoma agents, anti-depressants, and antiviral agents.

Each named drug should be understood to include the neutral form of the drug or pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs.

Exemplary drugs suitable for use in the nanoparticles include, but are not limited to, phosphodiesterase inhibitors, such as sildenafil and sildenafil citrate; HMG-CoA reductase inhibitors, such as atorvastatin, lovastatin, simvastatin, pravastatin, fluvastatin, rosuvastatin, itavastatin, nisvastatin, visastatin, atavastatin, bervastatin, compactin, dihydrocompactin, dalvastatin, fluindostatin, pitivastatin, and velostatin (also referred to as synvinolin); vasodilator agents, such amiodarone; antipsychotics, such as ziprasidone; calcium channel blockers, such as nifedipine, nicardipine, verapamil, and amlodipine; cholesteryl ester transfer protein (CETP) inhibitors; cyclooxygenase-2 inhibitors; microsomal triglyceride transfer protein (MTP) inhibitors; vascular endothelial growth factor (VEGF) receptor inhibitors; carbonic anhydrase inhibitors; and glycogen phosphorylase inhibitors. Other low-solubility drugs suitable for use in the nanoparticles are disclosed in US Published patent application 2005/0031692, herein incorporated by reference.

In one embodiment, the drug is ziprasidone or a pharmaceutically acceptable form thereof.

In another embodiment, the drug is a hydrophobic non-ionizable drug. By "hydrophobic non-ionizable drug" is meant a subclass of non-ionizable drugs that are essentially water insoluble and highly hydrophobic, and are characterized by a set of physical properties, as described hereinafter. By "non-ionizable" is meant that the drug has substantially no ionizable groups. By "ionizable groups" is meant functional groups that are at least about 10% ionized over at least a portion of the physiologically relevant pH range of 1 to 8. Such groups have pKa values of about 0 to 9. Thus, hydrophobic non-ionizable drugs do not have a pKa value between 0 and 9.

The first property of hydrophobic drugs is that they are extremely hydrophobic. Log P, defined as the base 10 logarithm of the ratio of the drug solubility in octanol to the drug solubility in water, is a widely accepted measure of hydrophobicity. By "extremely hydrophobic" is meant that the Log P value of the drug is at least 4.0, may be at least 4.5, and may be at least 5.0. Log P may be measured experimentally or calculated using methods known in the art. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (27 J. Chem. Inf. Comput. Sci. 21 (1987)); Viswanadhan's fragmentation method (29 J. Chem. Inf. Comput. Sci. 163 (1989)); or Broto's fragmentation method (19 Eur. J. Med. Chem.-Chim. Theor. 71 (1984). Preferably the Log P value is calculated by using the average value estimated using Crippen's, Viswanadhan's, and Broto's fragmentation methods.

The second property of hydrophobic drugs is that they have an extremely low solubility in water over the pH range of 6.5 to 7.5 at 25° C. By "extremely low solubility in water" is meant that the solubility of the drug in water is less than 100 μg/mL. Preferably, the hydrophobic drug has a water solubility of less than 50 μg/mL, and most preferably less than 10 μg/mL.

In another embodiment the drug is a cholesteryl ester transfer protein (CETP) inhibitor. CETP inhibitors are drugs that inhibit CETP activity. The effect of a drug on the activity of CETP can be determined by measuring the relative transfer ratio of radiolabeled lipids between lipoprotein fractions, essentially as previously described by Morton in *J. Biol. Chem.* 256, 11992, 1981 and by Dias in *Clin. Chem.* 34, 2322, 1988, and as presented in U.S. Pat. No. 6,197,786, the disclosures of which are herein incorporated by reference. The potency of CETP inhibitors may be determined by performing the above-described assay in the presence of varying concentrations of the test compounds and determining the concentration required for 50% inhibition of transfer of radiolabeled lipids between lipoprotein fractions. This value is defined as the "$IC_{50}$ value." Preferably, the CETP inhibitor has an $IC_{50}$ value of less than about 2000 nM, more preferably less than about 1500 nM, even more preferably less than about 1000 nM, and most preferably less than about 500 nM.

Specific examples of CETP inhibitors include [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester; (2R)-3-[[3-(4-chloro-3-ethylphenoxy)phenyl][[3-(1,1,2,2-tetrafluoroethoxy)phenyl]methyl]amino]-1,1,1-trifluoro-2-propanol; S-[2-([[1-(2-ethylbutyl)cyclohexyl]carbonyl]amino)phenyl]2-methylpropanethioate; trans-4-[[[2-[[[[3,5-bis(trifluoromethyl)phenyl]methyl](2-methyl-2H-tetrazol-5-yl)amino]methyl]-4-(trifluoromethyl)phenyl]ethylamino]methyl]-cyclohexaneacetic acid; trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl) acetic acid methanesulfonate; trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide; methyl N-(3-cyano-5-trifluoromethylbenzyl)-[6-(N'-cyclopentylmethyl-N'-ethylamino)indan-5-ylmethyl]-carbamate; methyl (3-cyano-5-trifluoromethylbenzyl)-[6-(N-cyclopentylmethyl-N-ethylamino)indan-5-ylmethyl]-carbamate; ethyl 4-((3,5-bis(trifluoromethyl)phenyl)(2-methyl-2H-tetrazol-5-yl)methyl)-2-ethyl-6-(trifluoromethyl)-3,4-dihydroquinoxaline-1(2H)-carboxylate; tert-butyl 5-(N-(3,5-bis(trifluoromethyl)benzyl)acetamido)-7-methyl-8-(trifluoromethyl)-2,3,4,5-tetrahydrobenzo[b]azepine-1-carboxylate; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl)-amino]-methyl}-4-trifluoromethyl-phenyl)-2-methyl-propyl]-piperidine-4-carboxylic acid; (3,5-bis-trifluoromethyl-benzyl)-[2-(1-methoxy-cycloheptyl)-5-trifluoromethyl-benzyl]-(2-methyl-2H-tetrazol-5-yl)-amine; (3,5-bis-trifluoromethyl-benzyl)-[2-(1-cyclohexyl-1-methoxy-ethyl)-5-trifluoromethyl-benzyl]-(2-methyl-2H-tetrazol-5-yl)-amine; the drugs disclosed in commonly owned U.S. patent application Ser. Nos. 09/918,127 and 10/066,091, the disclosures of both of which are incorporated herein by reference; and the drugs disclosed in the following patents and published applications, the disclosures of all of which are incorporated herein by reference: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; JP 11049743; WO 0018721; WO 0018723; WO 0018724; WO 0017164; WO 0017165; WO 0017166; EP 992496; EP 987251; WO 9835937; JP 03221376; WO 04020393; WO 05095395; WO 05095409; WO 05100298; WO 05037796; WO 0509805; WO 03028727; WO 04039364; WO 04039453; WO 0633002; and U.S. Provisional Patent Application Nos. 60/781,488 and 60/780,993, both of which were filed on Mar. 10, 2006.

Thus, in one embodiment, the CETP inhibitor is selected from the group of compounds mentioned above. In another embodiment, the CETP inhibitor is selected from the group consisting of (2R)-3-[[3-(4-chloro-3-ethylphenoxy)phenyl]

[[3-(1,1,2,2-tetrafluoroethoxy)phenyl]methyl]amino]-1,1,1-trifluoro-2-propanol; trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide amine; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl)-amino]-methyl}-4-trifluoromethyl-phenyl)-2-methyl-propyl]-piperidine-4-carboxylic acid; (3,5-bis-trifluoromethyl-benzyl)-[2-(1-methoxy-cycloheptyl)-5-trifluoromethyl-benzyl]-(2-methyl-2H-tetrazol-5-yl)-amine; (3,5-bis-trifluoromethyl-benzyl)-[2-(1-cyclohexyl-1-methoxy-ethyl)-5-trifluoromethyl-benzyl]-(2-methyl-2H-tetrazol-5-yl)-amine; and pharmaceutically acceptable forms thereof.

In still another embodiment, the CETP inhibitor is (2R)-3-[[3-(4-chloro-3-ethylphenoxy)phenyl][[3-(1,1,2,2-tetrafluoroethoxy)phenyl]methyl]amino]-1,1,1-trifluoro-2-propanol.

In still another embodiment, the CETP inhibitor is trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide.

In another aspect, the drug is an inhibitor of cyclooxygenase-2 (COX-2). COX-2 inhibitors are nonsteroidal anti-inflammatory drugs that exhibit anti-inflammatory, analgesic and antipyretic effects. Preferably, the COX-2 inhibitor is a selective COX-2 inhibitor, meaning that the drug is able to inhibit COX-2 without significant inhibition of cyclooxygenase-1 (COX-1). Preferably, the COX-2 inhibitor has a potency such that the concentration of drug that inhibits 50% of COX-2 enzyme in an in vitro test (i.e., the $IC_{50}$ value) is less than about 10 μM, preferably less than 5 μM, more preferably less than 2 μM. In addition, it is also preferable that the COX-2 inhibitor be selective relative to COX-1. Thus, preferably, the ratio of the $IC_{50,COX-2}$ to $IC_{50,COX-1}$ ratio for the compound is less than 0.5, more preferably less than 0.3, and most preferably less than 0.2.

Specific examples of COX-2 inhibitors include 4-(5-(4-methylphenyl)-3-(trifluoromethyl)-1H-pyrazol-1-yl)benzenesulfonamide (celecoxib); 4-(5-methyl-3-phenylisoxazol-4-yl)benzenesulfonamide (valdecoxib); N-(4-(5-methyl-3-phenylisoxazol-4-yl)phenylsulfonyl)propionamide (paracoxb); sodium (S)-6,8-dichloro-2-(trifluoromethyl)-2H-chromene-3-carboxylate; sodium (S)-7-tert-butyl-6-chloro-2-(trifluoromethyl)-2H-chromene-3-carboxylate; 2-[(2-chloro-6-fluorophenyl)amino]-5-methyl benzeneacetic acid (lumiracoxib); 4-(3-(difluoromethyl)-5-(3-fluoro-4-methoxyphenyl)-1H-pyrazol-1-yl)benzenesulfonamide (deracoxib); 4-(4-(methylsulfonyl)phenyl)-3-phenylfuran-2(5H)-one (rofecoxib); 5-chloro-2-(6-methylpyridin-3-yl)-3-(4-(methylsulfonyl)phenyl)pyridine (etoricoxib); 2-(3,4-difluorophenyl)-4-(3-hydroxy-3-methylbutoxy)-5-(4-(methylsulfonyl)phenyl)pyridazin-3(2H)-one; (Z)-3-((3-chlorophenyl)(4-(methylsulfonyl)phenyl)methylene)-dihydrofuran-2(3H)-one; N-(2-(cyclohexyloxy)-4-nitrophenyl)methanesulfonamide; 4-Methyl-2-(3,4-dimethylphenyl)-1-(4-sulfamoyl-phenyl)-1H-pyrrole; 6-((5-(4-chlorobenzoyl)-1,4-dimethyl-1H-pyrrol-2-yl)methyl)pyridazin-3(2H)-one; 4-(4-cyclohexyl-2-methyloxazol-5-yl)-2-fluorobenzenesulfonamide (tilmacoxib); 2-(4-Ethoxyphenyl)-4-methyl-1-(4-sulfamoyl-phenyl)-1H-pyrrole; 4-hydroxy-2-methyl-N-(5-methyl-2-thiazolyl)-2H-1,2-benzothiazine-3-carboxamide-1,1-dioxide (meloxicam); 4-(4-chloro-5-(3-fluoro-4-methoxyphenyl)-1H-pyrazol-1-yl)benzenesulfonamide (cimicoxib), and pharmaceutically acceptable forms thereof; and the compounds disclosed in the following patents and published applications, the disclosures of which are incorporated herein by reference: U.S. Pat. No. 5,466,823, U.S. Pat. No. 5,633,272, U.S. Pat. No. 5,932,598, U.S. Pat. No. 6,034,256, U.S. Pat. No. 6,180,651, U.S. Pat. No. 5,908,858, U.S. Pat. No. 5,521,207, U.S. Pat. No. 5,691,374, WO 99/11605, WO 98/03484, and WO 00/24719.

Preferably the COX-2 inhibitor is selected from the group consisting of celecoxib; valdecoxib; paracoxb; sodium (S)-6,8-dichloro-2-(trifluoromethyl)-2H-chromene-3-carboxylate; sodium (S)-7-tert-butyl-6-chloro-2-(trifluoromethyl)-2H-chromene-3-carboxylate; and pharmaceutically acceptable forms thereof. In one embodiment, the COX-2 inhibitor is celecoxib or pharmaceutically acceptable forms thereof.

Processes for Forming Nanoparticles

The nanoparticles may be formed by any process that results in formation of nanoparticles comprising non-crystalline drug and a polymer. The drug used to form the nanoparticles may be in a crystalline or non-crystalline form; however, at least 90 wt % of the drug in the resulting nanoparticles is in non-crystalline form.

One process for forming nanoparticles is an emulsification process. In this process, the drug and polymer are dissolved in an organic solvent that is immiscible with an aqueous solution in which the drug and polymer are poorly soluble, forming an organic solution. Solvents suitable for forming the solution of dissolved drug and polymers can be any compound or mixture of compounds in which the drug and the polymer are mutually soluble and which is immiscible in the aqueous solution. As used herein, the term "immiscible" means that the organic solvent has a solubility in the aqueous solution of less than about 10 wt %, preferably less than about 5 wt %, and most preferably less than about 3 wt %. Preferably, the organic solvent is also volatile with a boiling point of 150° C. or less. Exemplary organic solvents include methylene chloride, trichloroethylene, trichloro-trifluoroethylene, tetrachloroethane, trichloroethane, dichloroethane, dibromoethane, ethyl acetate, phenol, chloroform, toluene, xylene, ethyl-benzene, benzyl alcohol, creosol, methyl-ethyl ketone, methyl-isobutyl ketone, hexane, heptane, ether, and mixtures thereof. Preferred organic solvents are methylene chloride, ethyl acetate, benzyl alcohol, and mixtures thereof. The aqueous solution preferably is water.

Once the organic solution is formed, it is then mixed with the aqueous solution and homogenized to form an emulsion of fine droplets of the water immiscible organic solvent distributed throughout the aqueous phase. The volume ratio of organic solution to aqueous solution used in the process will generally range from 1:100 (organic solution:aqueous solution) to 2:3 (organic solution:aqueous solution). Preferably, the organic solution:aqueous solution volume ratio ranges from 1:9 to 1:2 (organic solution:aqueous solution). The emulsion is generally formed by a two-step homogenization procedure. The solution of drug, polymer, and organic solvent are first mixed with the aqueous solution using a rotor/stator or similar mixer to create a "pre-emulsion". This mixture is then further processed with a high-pressure homogenizer that subjects the droplets to very high shear, creating a uniform emulsion of very small droplets. A portion of the organic solvent is then removed forming a suspension of the nanoparticles in the aqueous solution.

Exemplary processes for removing the organic solvent include evaporation, extraction, diafiltration, pervaporation, vapor permeation, distillation, and filtration. Preferably, the organic solvent is removed to a level that is acceptable according to The International Committee on Harmonization (ICH) guidelines. Preferably, the concentration of organic solvent in the nanoparticle suspension is less than the solubility of the organic solvent in the aqueous solution. Even lower concentrations of organic solvent are preferred. Thus, the concentration of organic solvent in the nanoparticle suspension may be less than about 5 wt %, less than about 3 wt %, less than 1 wt %, and even less than 0.1 wt %.

An alternative process to form the nanoparticles is a precipitation process. In this process, the drug and polymer are first dissolved in an organic solvent that is miscible with an aqueous solution in which the drug and polymer are poorly soluble to form an organic solution. The organic solution is mixed with the aqueous solution causing the nanoparticles to precipitate. Organic solvents suitable for forming the organic solution of dissolved drug and polymers can be any compound or mixture of compounds in which the drug and the polymer are mutually soluble and which is miscible in the aqueous solution. Preferably, the organic solvent is also volatile with a boiling point of 150° C. or less. Exemplary organic solvents include acetone, methanol, ethanol, tetrahydrofuran (THF), and dimethylsulfoxide (DMSO). Mixtures of organic solvents, such as 50% methanol and 50% acetone, can also be used, as can mixtures with water, so long as the polymer and drug are sufficiently soluble to dissolve the drug and polymer. Preferred organic solvents are methanol, acetone, and mixtures thereof.

The aqueous solution may be any compound or mixture of compounds in which the drug and polymer are sufficiently insoluble so as to precipitate to form nanoparticles. The aqueous solution is preferably water.

The organic solution and aqueous solution are combined under conditions that cause solids to precipitate as nanoparticles. The mixing can be by addition of a bolus or stream of organic solution to a stirring container of the aqueous solution. Alternately a stream or jet of organic solution can be mixed with a moving stream of aqueous solution. In either case, the precipitation results in the formation of a suspension of nanoparticles in the aqueous solution.

For the precipitation process, the amount of drug and polymer in the organic solution depends on the solubility of each in the organic solvent and the desired ratios of drug to polymer in the resulting nanoparticles. The solution may comprise from about 0.1 wt % to about 20 wt % dissolved solids. A dissolved solids content of from about 0.5 wt % to 10 wt % is preferred.

The organic solution:aqueous solution volume ratio should be selected such that there is sufficient aqueous solution in the nanoparticle suspension that the nanoparticles solidify and do not rapidly agglomerate. However, too much aqueous solution will result in a very dilute suspension of nanoparticles, which may require further processing for ultimate use. Generally, the organic solution:aqueous solution volume ratio should be at least 1:100, but generally should be less than 1:2 (organic solution:aqueous solution). Preferably, the organic solution:aqueous solution volume ratio ranges from about 1:20 to about 1:3.

Once the nanoparticle suspension is made, a portion of the organic solvent may be removed from the suspension using methods known in the art. Exemplary processes for removing the organic solvent include evaporation, extraction, diafiltration, pervaporation, vapor permeation, distillation, and filtration. Preferably, the solvent is removed to a level that is acceptable according to ICH guidelines. Thus, the concentration of solvent in the nanoparticle suspension may be less than about 10 wt %, less than about 5 wt %, less than about 3 wt %, less than 1 wt %, and even less than 0.1 wt %.

Formation of Solid Compositions

The compositions of the present invention comprise nanoparticles comprising a drug and polymer, and a resuspending material. The resuspending material can be formulated with the nanoparticles either during the process used to form the nanoparticles or after the nanoparticles are formed.

In one embodiment, the resuspending material is formulated with the nanoparticles during the nanoparticle-formation process. In this embodiment, the resuspending material may be considered to be part of the nanoparticles. For the emulsion and precipitation processes described above, the resuspending material can be either added to the organic solution comprising the drug and polymer or added to the aqueous solution. In a preferred embodiment, the resuspending material is added to the aqueous solution. Formulating the resuspending material in the aqueous solution is advantageous as it allows the resuspending material to help reduce or eliminate flocculation or aggregation of the nanoparticles once they are formed.

In this embodiment, once the nanoparticles are formed, the resulting mixture comprises the nanoparticles suspended in the aqueous solution, which also comprises the resuspending material. Preferably, the resuspending material is dissolved in the aqueous solution. The liquids are then removed from the aqueous solution, as discussed below, resulting in a solid composition comprising the nanoparticles and the resuspending material.

In another embodiment, the resuspending material is formulated with the nanoparticles in suspension after the nanoparticles have been formed. This has advantages when the process for removing the organic solvent from the nanoparticle suspension would also remove a portion of the resuspending material (e.g., diafiltration). This embodiment is also preferred when processes are used to increase the concentration of nanoparticles in the suspension. Generally, in this embodiment, the resuspending material is added to the suspension containing the nanoparticles. The resuspending material is preferably dissolved in the aqueous suspension containing the nanoparticles. The liquids are then removed from the aqueous solution, resulting in a solid composition comprising the nanoparticles and the resuspending material.

Thus, a process for forming a solid composition comprises: (a) forming an organic solution comprising a poorly water soluble drug and a poorly aqueous soluble polymer dissolved in an organic solvent, wherein the drug has a solubility in water of less than 5 mg/ml over the pH range of 6.5 to 7.5; (b) forming an aqueous solution, wherein the drug and the polymer are poorly soluble in the aqueous solution; (c) mixing the organic solution with the aqueous solution to form a first mixture; (d) removing the organic solvent from the first mixture to form a suspension comprising the nanoparticles and the aqueous solution, wherein (i) the nanoparticles have an average size of less than 500 nm, and (ii) at least 90 wt % of the drug in the nanoparticles is non-crystalline; (e) adding a resuspending material selected from HPMCAS, CMEC, or pharmaceutically acceptable salts thereof to either the aqueous solution of step (b) or to the suspension of step (d), wherein the resuspending material constitutes from 5 wt % to 90 wt % of the combined mass of (1) the resuspending material and (2) the nanoparticles; and (f) removing liquid from the suspension to form a solid composition comprising the nanoparticles and the resuspending material.

Essentially any process that removes the liquid from the suspension may be used to form a solid composition, provided the process does not affect the properties of the nanoparticles or the resuspending material. Exemplary processes include spray drying, spray coating, spray layering, lyophylization, evaporation, vacuum evaporation, and filtration. A preferred process is spray drying. Another preferred process is lyophylization. One or more processes may be combined to remove the liquid from the suspension and yield a solid composition. For example, a portion of the liquid may be removed by filtration to concentrate the suspension, followed by spray-drying to remove most of the remaining liquids, followed by a further drying step such as tray-drying.

Following removal of the liquid, the nanoparticles and resuspending material are collectively present in the resulting solid composition in an amount ranging from about 60 wt % to 100 wt % of the total mass of the composition. Preferably, the nanoparticles and resuspending material collectively constitute at least 70 wt %, more preferably at least 80 wt %, and even more preferably at least 90 wt % of the composition. In one embodiment, the composition consists essentially of the nanoparticles and the resuspending material. By "consists essentially of" is meant that the composition contains less than 1 wt % of any other excipients and that any such excipients have no affect on the performance or properties of the composition. This material may then be incorporated into a dosage form containing other excipients.

In one embodiment, the poorly aqueous soluble polymer is ethyl cellulose and the resuspending material is a salt form of HPMCAS.

In another embodiment, the poorly aqueous soluble polymer is ethyl cellulose and the resuspending material is a salt form of CMEC.

In another embodiment, the nanoparticle comprises ethyl cellulose and an ionizable surface stabilizer.

The presence of nanoparticles in the solid composition can be determined using the following procedure. A sample of the solid composition is embedded in a suitable material, such as an epoxy or polyacrylic acid (e.g., LR White from London Resin Co., London, England). The sample is then microtomed to obtain a cross-section of the solid composition that is about 100 to 200 nm thick. This sample is then analyzed using transmission electron microscopy (TEM) with energy dispersive X-ray (EDX) analysis. TEM-EDX analysis quantitatively measures the concentration and type of atoms larger than boron over the surface of the sample. From this analysis, regions that are rich in drug and polymer can be distinguished from regions that are rich in the resuspending material. The size of the regions that are rich in drug and polymer will have an average diameter of less than 500 nm in this analysis, demonstrating that the solid composition comprises nanoparticles of drug and polymer, and the resuspending material. See, for example, Transmission Electron Microscopy and Diffractometry of Materials (2001) for further details of the TEM-EDX method.

Another procedure that demonstrates the solid composition contains nanoparticles is to administer a sample of the solid composition to water to form a suspension of the nanoparticles. The suspension is then analyzed by dynamic light scattering (DLS) as described herein below. A solid composition of the invention will form nanoparticles having an average cumulant diameter of less than 500 nm.

A specific procedure for demonstrating the solid composition contains nanoparticles is as follows. A sample of the solid composition is added to an aqueous solution at ambient temperature at a pH greater than 6, preferably pH 6.5. An appropriate aqueous solution is phosphate buffered saline solution (PBS) at pH 6.5. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. The sample is added such that the concentration of solids is less than about 1 mg/mL. The so-formed suspension is then analyzed by DLS. The solid composition contains nanoparticles if the DLS analysis results in particles having an average cumulant diameter of less than 500 nm.

A solid composition of the invention will show the presence of nanoparticles in at least one, and preferably both of the above tests.

The solid compositions of the invention may be present in a variety of forms, including particles, granules, powders, dust, pellets, flakes, slabs, rods, and tablets. Preferably, the solid compositions of the present invention are in the form of small particles, granules, or powders. The small particles, granules, or powders may be formed in the process of making the solid composition, or may be formed subsequent to formation of the solid composition.

Once the solid composition is formed, it may be desirable to adjust the size of the particles of the solid composition. Some of the processes described above, such as spray drying, produce small particles of the solid composition that may not require further processing. Other processes used to form the solid composition may result in larger particles, sheets, flakes, or other forms of the solid composition. Thus, the particle size of the solid composition may be adjusted using various techniques known in the art, such as through the use of grinders and mills. In other cases, it may be desirable to increase the size of the resulting particles, using various granulation techniques. See, for example, *Remington: The Science and Practice of Pharmacy*, $20^{th}$ Edition (2000).

Preferably, the solid composition of the invention is in the form of particles, granules, or powders having a mean diameter ranging from about 1 μm to about 500 μm. For improved processing of the solid composition, larger particles or granules are generally preferred. Thus, the mean diameter of the solid composition is preferably at least 1 μm, more preferably at least 10 μm, or even more preferably at least 25 μm. However, if the particles or granules are too large, the rate of dissolution of the solid composition can be affected. Thus, the mean diameter may be less than 500 μm, or less than 100 μm in diameter. The mean diameter of the solid composition preferably ranges from 10 μm to 500 μm, more preferably from 25 μm to 100 μm.

The solid compositions of the present invention, when administered to an aqueous solution, form a suspension of nanoparticles. The ability of the solid composition to form a nanoparticle suspension when administered to an aqueous solution can be determined using the following procedures. In the first procedure, the average particle size of the nanoparticle suspension is determined as follows. The solid composition is added to an aqueous solution, such as water or PBS, to form a suspension such that the concentration of solids is less than about 1 mg/mL. The average particle size of the nanoparticles formed in the suspension is then determined by dynamic light scattering (DLS) techniques.

In a preferred embodiment, when a solid composition of the invention is administered to an aqueous solution using such a test, the average particle size of the nanoparticles formed in the resulting suspension, as determined by DLS, is at least 50% and no more than 200% the average particle size of the nanoparticles prior to formation of the solid composition. Preferably, the solid composition provides an average particle size that is at least 67% and no more than 150% the average particle size prior to formation of the solid composition. Even more preferably, the solid composition provides an average particle size that is at least 75% and no more than 133% the average particle size prior to formation of the solid composition.

The second procedure is known as a filter potency test. In this test the concentration of drug after passing the suspension of the nanoparticles through a filter is determined. The solid composition is added to an aqueous solution as described above. The concentration of drug in the so-formed suspension is then determined using standard techniques, such as by high-performance liquid chromatography (HPLC). Next, the suspension is filtered through a filter, and the concentration of drug in the filtered sample is determined via standard techniques. A loss in potency after filtering a sample through a filter is an indication that the nanoparticles in the sample are larger than the filter pore size. Exemplary filters that can be used in this test include a 1-μm glass fiber filter, a 0.45-μm syringe filter, and a 0.2-μm syringe filter. One skilled in the art will understand that the pore size and material of the filter should be selected to ensure the nanoparticles are not retained on the filter. Generally, the pore size of the filter and the range of nanoparticle average diameters are given as follows:

| Filter Pore Size (μm) | Suitable Range of Nanoparticle Diameters (nm) |
| --- | --- |
| 1 | >250 |
| 0.45 | 150 to 300 |
| 0.2 | <200 |

Preferably, the ratio of the concentration of drug in the filtered sample is at least 60% the concentration of drug in the unfiltered sample. Preferably, the concentration of drug in the filtered sample is at least 70% the concentration of drug in the unfiltered sample. Most preferably, the concentration of drug in the filtered sample is at least 80% the concentration of drug in the unfiltered sample.

Dosage Forms

The compositions of the present invention may be administered using any known dosage form. The dosage form may contain conventional excipients in addition to the nanoparticles and resuspending material, such as binders, fillers, disintegrants, diluents, surfactants, and/or coatings. In one embodiment, the compositions are designed for oral administration. Exemplary oral dosage forms include: powders or granules; tablets; chewable tablets; capsules; unit dose packets, sometimes referred to in the art as "sachets" or "oral powders for constitution" (OPC); syrups; and suspensions. One skilled in the art will recognize other suitable dosage forms and methods for administration of the compositions of the invention.

In one embodiment, the compositions of the present invention are capable of improving the concentration of dissolved drug in a use environment relative to a control composition consisting essentially of the drug alone without any polymer or resuspending material. In order to determine concentration enhancement in vitro, the amount of "free" drug, or solvated drug is measured. By "free" drug is meant drug which is in the form of dissolved drug or present in micelles, but which is not in the nanoparticles or any solid particles larger than 500 nm, such as precipitate. A composition of the invention provides concentration enhancement if, when administered to an aqueous use environment, it provides a free drug concentration that is at least 1.25-fold the free drug concentration provided by the control composition. Preferably, the free drug concentration provided by the compositions of the invention are at least about 1.5-fold, more preferably at least about 2-fold, and most preferably at least about 3-fold that provided by the control composition.

Alternatively, the compositions of the present invention, when dosed orally to a human or other animal, provide an AUC in drug concentration in the blood plasma or serum (or relative bioavailability) that is at least 1.25-fold that observed in comparison to the control composition. Preferably, the blood AUC is at least about 2-fold, more preferably at least about 3-fold, even more preferably at least about 4-fold, still more preferably at least about 6-fold, yet more preferably at least about 10-fold, and most preferably at least about 20-fold that of the control composition. The determination of AUCs is a well-known procedure and is described, for example, in Welling, "Pharmacokinetics Processes and Mathematics," ACS Monograph 185 (1986).

Alternatively, the compositions of the present invention, when dosed orally to a human or other animal, provide a maximum drug concentration in the blood plasma or serum ($C_{max}$) that is at least 1.25-fold that observed in comparison to the control composition. Preferably, the $C_{max}$ is at least about 2-fold, more preferably at least about 3-fold, even more preferably at least about 4-fold, still more preferably at least about 6-fold, yet more preferably at least about 10-fold, and most preferably at least about 20-fold that of the control composition. Thus, compositions that meet the in vitro or in vivo performance criteria, or both, are considered to be within the scope of the invention.

Without further elaboration, it is believed that one of ordinary skill in the art can, using the foregoing description, utilize the present invention to its fullest extent. Therefore, the following specific embodiments are to be construed as merely illustrative and not restrictive of the scope of the invention. Those of ordinary skill in the art will understand that variations of the conditions and processes of the following examples can be used.

EXAMPLES

Drugs Used in Examples

The following drugs were used in the examples described below.

Drug 1 was 4-[5-(4-methylphenyl)-3-(trifluoromethyl)-1H-pyrazol-1-yl]benzenesulfonamide, also known as celecoxib, having the structure:

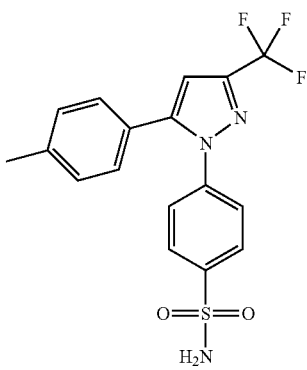 [SMILES: Cc1ccc(-c2cc(C(F)(F)F)nn2-c2ccc(S(N)(=O)=O)cc2)cc1]

Drug 1 has a solubility in MFD solution of about 40 μg/mL, and a Log P value of 3.75. The $T_m$ of Drug 1 is 158° C., and the $T_g$ of amorphous Drug 1 was determined by DSC analysis to be 54° C.

Drug 2 was [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, also known as torcetrapib, having the structure:

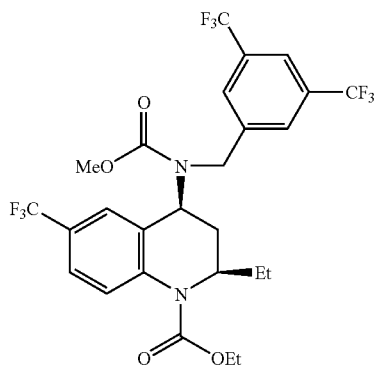 [SMILES: CCOC(=O)N1c2ccc(C(F)(F)F)cc2[C@@H](N(Cc2cc(C(F)(F)F)cc(C(F)(F)F)c2)C(=O)OC)C[C@H]1CC]

Drug 2 has a solubility in water of less than 0.1 μg/mL, and a CLog P value of 7.6. The $T_m$ of Drug 2 is 99° C., and the $T_g$ was determined by DSC analysis to be 29° C.

Poorly Aqueous Soluble Polymer

Ethylcellulose was used as the poorly aqueous soluble polymer in the examples. Specifically, the ethylcellulose used was ETHOCEL® Viscosity 4, Dow Chemical Co., Midland, Mich.

The ethylcellulose was evaluated using the following procedure to determine its aqueous solubility. First, 0.2 mg/mL of the polymer was added to a PBS solution consisting of 20 mM $Na_2HPO_4$, 47 mM $KH_2PO_4$, 87 mM NaCl, and 0.2 mM KCl, adjusted to pH 6.5 with NaOH. The polymer was stirred in the PBS solution for approximately 1 hour at room temperature. Next, the polymer solution was filtered through a nylon 0.45 μm filter that had been weighed dry prior to filtration. The filter was dried overnight at 40° C., and weighed the following morning. The amount of soluble polymer was calculated from the amount of polymer added to form the polymer solution minus the amount of polymer remaining on the filter. The results of these tests showed that less than 0.001 mg/mL of the ethylcellulose was soluble at pH 6.5. Thus, ethylcellulose is poorly aqueous soluble.

Example 1

For Example 1, nanoparticles containing Drug 1 were prepared as follows. First, 2.4 g Drug 1 and 3 g ethylcellulose were dissolved in 50 mL methylene chloride to form an organic solution. Next, 0.6 g sodium taurocholate (NaTC) was dissolved in 150 mL deionized water to form an aqueous solution. The organic solution was then poured into the aqueous solution and emulsified for 5 min using a Kinematica Polytron 3100 rotor/stator (Kinematica AG, Lucerne, Switzerland) at 10,000 rpm (high-shear mixing). The solution was further emulsified using a Microfluidizer (Microfluidics [Newton, Mass.] model M-110S F12Y with ice bath and cooling coil), for 15 minutes (high-pressure homogenization). The methylene chloride was removed from the emulsion using a rotary evaporator, resulting in an aqueous suspension of nanoparticles, with a composition ratio of 4:5:1 Drug 1:ethylcellulose:NaTC.

Light Scattering Analysis

The particle size of the nanoparticles in the aqueous suspension was determined using dynamic light scattering (DLS) as follows. The aqueous suspension was filtered using a 1 μm filter and poured into a cuvette. Dynamic light-scattering was measured using a Brookhaven Instruments (Holtsville, N.Y.) BI-200SM particle size analyzer with a BI-9000AT correlator. The sums of exponentials from the autocorrelation functions are analyzed to extract size distributions from the samples, and the size is reported as the cumulant value. The average diameter was found to be 56 nm, with a polydispersity of 0.12.

Isolation of Solid Composition

A solid composition of the invention was prepared as follows. The above nanoparticle suspension was mixed with the ammonium salt of hydroxypropyl methylcellulose acetate succinate (HPMCAS; AQOAT-L, available from Shin Etsu, Tokyo, Japan), and spray dried to form a solid composition. The HPMCAS ammonium salt was formed by dissolving 100 mg HPMCAS-L in 5 mL buffer containing 0.05 g ammonium carbonate adjusted to pH 5.5 with glacial acetic acid. To obtain the spray solution, the aqueous nanoparticle suspension was diluted to 20 mg/mL solids using deionized water, and 5 mL diluted nanoparticle suspension was added to 5 mL HPMCAS solution. The spray suspension was pumped to a small-scale spray-drying apparatus, at a liquid feed rate of 0.15 ml/min. Heated gas entered the drying chamber at an inlet temperature of 120° C., with a flow of 1 standard $ft^3$/min (SCFM). The resulting solid composition was collected on a 0.8 μm nylon filter, and had a mass ratio of 4:5:1:10 Drug 1:ethylcelluose:NaTC:HPMCAS-L, ammonium salt.

Filter Potency

A filter-potency test was then used to characterize the nanoparticle suspension of Example 1. Filter potency tests are used to examine changes in nanoparticle suspension potencies due to particle agglomeration. As nanoparticles agglomerate, the larger particles are removed via filtration, and the concentration of suspended drug is reduced.

The solid composition of Example 1 was added to an aqueous solution to form a nanoparticle suspension as follows. A 25-mg sample of the solid composition was added to 5 mL phosphate buffered saline (PBS) solution containing 20 mM Na$_2$HPO$_4$, 47 mM KH$_2$PO$_4$, 87 mM NaCl, and 0.2 mM KCl, adjusted to pH 6.5 with NaOH. The solution was stirred and samples were taken after 30 minutes. To measure potency, a sample of the aqueous nanoparticle suspension was diluted 1:5 with methanol and analyzed by high-performance liquid chromatography (HPLC). Next, the suspensions were filtered using a 0.2 μm filter and analyzed again using HPLC.

HPLC analysis of Drug 1 was performed using a Zorbax SB C$_8$ column. The mobile phase consisted of 55% acetonitrile/45% 50 mM triethylamine, adjusted to pH 7. Ultraviolet (UV) absorbance was measured at 254 nm.

Potencies of the nanoparticle suspensions are shown in Table 1. The results in Table 1 show that 72% of the potency of the nanoparticle suspension of Example 1 is maintained following filtration by a 0.2 μm filter. This indicates that most of the nanoparticles of the invention remain small and unagglomerated following administration of the solid composition of Example 1 to an aqueous solution.

TABLE 1

| Sample | Potency Unfiltered (μg/mL) | Potency 0.2 μm filtered (μg/mL) | Potency filtered/ unfiltered (%) |
|---|---|---|---|
| Example 1 | 1010 | 730 | 72 |

Example 2

For Example 2, an aqueous nanoparticle suspension containing Drug 1 was prepared as described for Example 1. A solid composition of the invention was formed by spray drying the nanoparticle suspension together with the sodium salt form of HPMCAS-L, Fraction 4. To fractionate the HPMCAS, 10 g HPMCAS was added to 200 mL acetone and stirred. To isolate fraction 1, 100 mL water was added, the solution was centrifuged at 15,000 rpm for 3 minutes, and the solid precipitate (Fraction 1) was removed. To isolate Fraction 2, an additional 50 mL water was added to the solution and centrifuged, and the precipitate (Fraction 2) removed. Fraction 3 was obtained by further adding 50 mL water to the solution (for a total of 200 mL water and 200 mL acetone solution), and centrifuging to remove the precipitate (Fraction 3). Finally, Fraction 4 was obtained by removing the liquids by roto-evaporation, dissolving the resulting solids in acetone, and precipitating the solution in hexane to form large particles of polymer. The particles of polymer were then collected by decantation and dried under vacuum, yielding 2.34 g Fraction 4. To obtain the sodium salt of HPMCAS Fraction 4, 1 g HPMCAS Fraction 4 was added to 50 mL water and stirred, and the pH was adjusted to 7 using 1 N NaOH.

To obtain the solid composition of Example 2, 30 mL aqueous nanoparticle suspension was diluted to 50 mL with water, and added to 50 mL of the HPMCAS Fraction 4, sodium salt solution. The nanoparticles were spray-dried as follows. The spray suspension was pumped to a spray drier (a Niro type XP Portable Spray-Drier with a Liquid-Feed Process Vessel ("PSD-1")), equipped with a pressure nozzle (Schlick 1.0; Dusen Schlick, GmbH of Untersiemau, Germany). The PSD-1 was equipped with 9-inch and 4-inch chamber extensions. The spray suspension was pumped to the spray drier at about 20 g/min at a pressure of 200 psig. Drying gas (nitrogen) was circulated at an inlet temperature of 120° C. The evaporated liquids and drying gas exited the spray drier at a temperature of 50° C. The resulting solid composition was collected in a cyclone, and had a mass ratio of 4:5:1:10 Drug 1:ethylcellulose:NaTC:HPMCAS-L, Fraction 4, sodium salt.

Filter Potency

A 15-mg sample of the solid composition of Example 2 was added to 3 mL PBS, and stirred for about 45 minutes. To measure nanoparticle potency, a sample of the aqueous nanoparticle suspension was diluted 1:5 v/v with 80/20 v/v methanol/water and analyzed by HPLC. Next, the suspensions were filtered using a 0.2 μm filter and analyzed again using HPLC.

Potencies of the nanoparticle suspensions are shown in Table 2. The results in Table 2 show that 94% of the potency of the nanoparticle suspension of Example 2 is maintained following filtration by a 0.2 μm filter. This indicates that most of the nanoparticles of the invention remain small and unagglomerated following administration of the dry, solid composition to an aqueous solution.

TABLE 2

| Sample | Potency Unfiltered (μg/mL) | Potency 0.2 μm filtered (μg/mL) | Potency filtered/ unfiltered (%) |
|---|---|---|---|
| Example 2 | 1100 | 1040 | 94 |

A filter potency transfer test was also used to characterize the solid composition of Example 2 following administration to a model gastric solution. A 20-mg sample of the solid composition was added to 2 mL model gastric solution containing 0.1 N HCl, and vortexed for 30 seconds. The solution was stirred for an additional 29% minutes, then 2 mL of modified PBS (2 times the standard concentration, with a pH of 10.7) was added to obtain a final pH of 6.5. The solution was stirred, and sampled after 30 minutes in the modified PBS. To measure nanoparticle potency, a sample of the aqueous nanoparticle suspension was diluted 1:5 v/v with methanol and analyzed by HPLC. Next, the suspensions were filtered using a 0.2 μm filter and analyzed again using HPLC.

Potencies of the nanoparticle suspensions are shown in Table 3. The results in Table 3 show that 91% of the potency of the nanoparticle suspension of Example 2 is maintained following filtration by a 0.2 μm filter. This indicates that the nanoparticle suspension of Example 2 is stable to exposure to gastric solution.

TABLE 3

| Sample | Potency Unfiltered (μg/mL) | Potency 0.2 μm filtered (μg/mL) | Potency filtered/ unfiltered (%) |
|---|---|---|---|
| Example 2 | 1003 | 909 | 91 |

Example 3

For Example 3, an aqueous suspension of nanoparticles containing Drug 2 were prepared using the procedures outline in Example 1 with the following exceptions. The organic solution consisted of 160 mg Drug 2 and 160 mg ethylcellulose dissolved in methylene chloride, while the aqueous solution consisted of 80 mg NaTC was dissolved in 20 mL deionized water. The organic solution was then poured into the aqueous solution and emulsified for 3 min using high-shear mixing. The solution was further emulsified for 6 minutes using high-pressure homogenization. The methylene chloride was removed from the emulsion using a rotary evaporator, resulting in an aqueous suspension of nanoparticles, with a mass ratio of 2:2:1 Drug 2:ethylcellulose:NaTC.

Light Scattering Analysis

The particle size of the nanoparticles in the aqueous suspension was determined using dynamic light scattering (DLS) as described above. The average cumulant diameter was found to be 106 nm, with a polydispersity of 0.15.

Isolation of Solid Composition

A solid composition of the invention was prepared as follows. First, 1 g ammonium carbonate was dissolved in 100 mL water and the pH was adjusted to 6:5 with glacial acetic acid. A 500-mg sample of HPMCAS-L was then added to this solution to obtain a 5 mg/mL solution of HPMCAS-L ammonium salt.

To obtain the solid composition of Example 3, 5 mL of the aqueous nanoparticle suspension described above was added to 10 mL of the HPMCAS-L ammonium salt solution. The resulting solution was then spray-dried, as described in Example 1. The resulting solid composition was collected on a 0.8 μm nylon filter, and had a mass ratio of 2:2:1:5 Drug 2:ethylcellulose:NaTC:HPMCAS-L, ammonium salt.

Filter Potency

A 10-mg sample of the solid composition of Example 3 was added to 0.5 mL water, followed by 4.5 mL model gastric solution. The solution was stirred for 29% minutes, then 5 mL of modified PBS was added to obtain a final pH of 6.5. The solution was stirred, and sampled after 20 minutes in modified PBS. To measure nanoparticle potency, a sample of the aqueous nanoparticle suspension was diluted 1:5 by volume with 8:2 methanol:water v/v and analyzed by HPLC. Next, the suspensions were filtered using a 0.2 μm filter and analyzed again using HPLC.

Potencies of the nanoparticle suspensions are shown in Table 5. The results in Table 5 show that 77% of the potency of the nanoparticle suspension of Example 3 is maintained following filtration by a 0.2 μm filter. This indicates that the nanoparticle suspension of Example 3 is stable to exposure to gastric solution.

TABLE 5

| Sample | Potency Unfiltered (μg/mL) | Potency 0.2 μm filtered (μg/mL) | Potency filtered/unfiltered (%) |
|---|---|---|---|
| Example 3 | 184 | 142 | 77 |

Control 1

For Control 1, a large batch of nanoparticles containing Drug 2 was prepared as follows. First, 2000 mg Drug 2 and 2000 mg ethylcellulose were dissolved in 125 mL methylene chloride to form an organic solution. Next, 1000 mg NaTC was dissolved in 500 mL deionized water to form an aqueous solution. The organic solution was then poured into the aqueous solution and emulsified for 5 min using high-shear mixing, and further emulsified using high-pressure homogenization for 20 minutes. The methylene chloride was removed from the emulsion using a rotary evaporator, resulting in an aqueous suspension of nanoparticles, with a mass ratio of 2:2:1 Drug 2:ethylcellulose:NaTC.

Isolation of Solid Composition

For formation of a solid composition of Control 1, first, 30/35 mesh nonpareil sugar spheres were seal-coated with ethylcellulose (about 5 wt % coating/(coating plus core). Next, 4.5 g trehalose was added to 445.5 g of the aqueous nanoparticle suspension above (in 3 batches), and the suspension was coated onto 50 g of sealed sugar spheres using a Mini-Glatt fluid bed coater equipped with a Würster column insert. The suspension was sprayed at a rate of about 3.5 g/min, the inlet temperature was 65° C., and the atomizing air pressure was 1.5 bar. After 13 wt % of the solid composition had been added (solids/(solids+core)), the coated cores were dried with the fluidizing gas. The composition of Control 1 consisted of 2:2:1:5 Drug 2:Ethocel:NaTC:trehalose by mass, coated on sucrose cores.

Filter Potency

A 3.8 g sample of Control 1 was added to 5 mL water and vortexed for 30 seconds. The sample slurry was added to a 100 mL VanKel dissolution flask containing 45 mL 0.1N HCl. The flask was stirred at 100 rpm. After 29 minutes, modified PBS was added to obtain a final pH of 6.5 and volume of 100 mL. Samples were removed from the flask after 30 minutes in modified PBS, using a 1 mL pipettman. An aliquot of the unfiltered sample was diluted for HPLC analysis, and the sample was filtered through a 0.2 μm filter and an aliquot was diluted for HPLC analysis. Each aliquot was diluted 1:5 with 80/20 methanol/water.

Potencies of the nanoparticle suspensions are shown in Table 6. The results in Table 6 show that only about 1% of the potency of the nanoparticle suspension of Control 1 is maintained following filtration by a 0.2 μm filter.

TABLE 6

| Sample | Potency Unfiltered (μg/mL) | Potency 0.2 μm filtered (μg/mL) | Potency 0.2 μm filtered/unfiltered (%) |
|---|---|---|---|
| Control 1 | 554 | 7 | 1 |

Example 4

For Example 4, nanoparticles containing Drug 1 were prepared using the procedures outlined in Example 1 with the following exceptions. The organic solution consisted of 2400 mg Drug 1 and 3000 mg ethylcellulose dissolved in methylene chloride, while the aqueous solution consisted of 600 mg NaTC was dissolved in 150 mL deionized water to form an aqueous solution. The organic solution was then poured into the aqueous solution and emulsified for 6 min using high-shear mixing, followed by high-pressure homogenization for 7 minutes. The methylene chloride was removed from the emulsion using a rotary evaporator, resulting in an aqueous suspension of nanoparticles, with a mass ratio of 4:5:1 Drug 1:ethylcellulose:NaTC.

Light Scattering Analysis

The particle size of the nanoparticles in the aqueous suspension was determined using dynamic light scattering (DLS) as described above. The average cumulant diameter was found to be 58 nm, with a polydispersity of 0.16.

Isolation of Solid Composition

A solid composition of the invention was prepared using the following procedure. First, 1 g of carboxymethyl ethylcellulose (CMEC, available from Freund Industrial Co., Ltd., Japan) was dissolved in 50 mL water and the pH was adjusted to 7 with 1 N NaOH, forming the sodium salt form of CMEC. Next, 40 mL aqueous nanoparticle suspension above and 10 mL deionized water were added to 50 mL CMEC, sodium salt solution. The resulting suspension was spray-dried using the PSD-1 spray-drier, as described for Example 2, except that the inlet temperature was 110° C. Example 4 had a mass ratio of 20:25:5:50 Drug 1:ethylcellulose:NaTC:CMEC, sodium salt.

Filter Potency

A 50 mg sample of the solid composition of Example 4 was added to 5 mL model gastric solution and stirred for 29½ minutes. To this suspension was then added 5 mL of modified PBS. The solution was sampled after 30 minutes in modified PBS. To measure nanoparticle potency, a sample of the aqueous nanoparticle suspension was diluted 1:5 with methanol and analyzed by HPLC. Next, the suspensions were filtered using a 0.2 μm filter and analyzed again using HPLC.

Potencies of the nanoparticle suspensions are shown in Table 7. The results in Table 7 show that 90% of the potency of the nanoparticle suspension of Example 4 is maintained following filtration by a 0.2 μm filter. This indicates that the nanoparticle suspension of Example 4 is stable to exposure to gastric solution.

TABLE 7

| Sample | Potency Unfiltered (μg/mL) | Potency 0.2 μm filtered (μg/mL) | Potency filtered/ unfiltered (%) |
|---|---|---|---|
| Example 4 | 1040 | 910 | 90 |

Examples 5-8

For Examples 5-8, nanoparticles containing Drug 1 were prepared as follows. First, 12.8 g Drug 1 and 16.0 g ethylcellulose were dissolved in 82.892 gm ethyl acetate to form an organic solution. Next, 3.2 g sodium taurocholate (NaTC) was dissolved in 368 mL deionized water to form an aqueous solution. The organic solution was then poured into the aqueous solution and emulsified for 2 min using a Silverson (East Longmeadow, Mass.) rotor/stator at 10,000 rpm (high-shear mixing). The solution was further emulsified using a Microfluidizer (Microfluidics [Newton, Mass.] model M-110), for 25 minutes (high-pressure homogenization). The ethyl acetate was removed from the emulsion using a rotary evaporator, resulting in an aqueous suspension of nanoparticles, with a composition ratio of 4:5:1 Drug 1:ethylcellulose:NaTC.

Light Scattering Analysis

The particle size of the nanoparticles in the aqueous suspension was determined using dynamic light scattering (DLS) as follows. The aqueous suspension was diluted 50:1 using distilled water and poured into a cuvette. Dynamic light-scattering was measured using a Brookhaven Instruments (Holtsville, N.Y.) Fiber Optic Quasi Elastic Light Scattering (FOQELS) Particle Size Analyzer. The average diameter was found to be 151 nm, with a polydispersity of 0.12.

Isolation of Solid Composition

Solid compositions of the invention were prepared as follows. First, a stock solution of carboxymethyl ethylcellulose (CMEC) was prepared by first adding 16 gm CMEC to 184 gm distilled water. The solution was then adjusted to pH 10 by drop-wise addition of 25 wt % NaOH to allow the polymer to dissolve.

Samples of the CMEC-Na solution were then mixed with samples of the nanoparticle suspension, as shown in Table 8.

TABLE 8

| Example | Volume of Nanoparticle Suspension (mL) | Volume of CMEC-Na Solution (mL) | Amount of CMEC-Na Salt Relative to the Combined Mass of Nanoparticles and CMEC-Na Salt (wt %) |
|---|---|---|---|
| 5 | 50 | 50 | 50 |
| 6 | 60 | 40 | 40 |
| 7 | 75 | 25 | 25 |
| 8 | 80 | 20 | 20 |

The resulting nanoparticle suspensions were then spray dried using the procedures described in Example 1, resulting in the formation of solid compositions of the present invention.

Filter Potency

The solid compositions of Examples 5-8 were added separately at a concentration of 1 mg/mL to PBS and filter potency was determined as described in Example 1. Potencies of the nanoparticle suspensions are shown in Table 9. The results in Table 9 show that 79% or more of the potency of the nanoparticle suspensions of Examples 4-8 are maintained following filtration by a 0.2 μm filter. This indicates that most of the nanoparticles of the invention remain small and unagglomerated following administration of the solid composition to an aqueous solution.

TABLE 9

| Sample | Potency Unfiltered (μg/mL) | Potency 0.2 μm filtered (μg/mL) | Potency filtered/ unfiltered (%) |
|---|---|---|---|
| Example 5 | 184 | 153 | 83 |
| Example 6 | 186 | 150 | 81 |
| Example 7 | 184 | 145 | 79 |
| Example 8 | 184 | 146 | 79 |
| Control 2 | 196 | 30 | 15 |

Control 2

As a control, a 50-gm sample of the nanoparticle suspension described for Examples 5-8 was mixed with a 50-gm sample of 8 wt % trehalose dissolved in water. The resulting suspension was spray dried as described in Examples 5-8 to form a solid composition having a mass ratio of trehalose to nanoparticles of 1:1.

A filter-potency test was performed on the solid composition of Control 2 using the procedures described for Examples 5-8. The results of these tests, presented in Table 9, show that only 15% of the nanoparticles of Control 2 passed through the 0.2-μm filter, indicating that considerable agglomeration of the nanoparticles had occurred.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A solid pharmaceutical composition comprising:
    (a) nanoparticles comprising a poorly water soluble drug distributed throughout a poorly aqueous soluble polymer selected from the group consisting of ethylcellulose, propylcellulose, butylcellulose, cellulose acetate, cellulose propionate, cellulose butyrate, cellulose acetate propionate, cellulose acetate butyrate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, hydroxypropyl methylcellulose butyrate, poly(vinyl acetate-co-vinyl alcohol), poly(ethylene-co-vinyl acetate), poly(ethyl acrylate-co-methyl methacrylate), poly(lactide), poly(glycolide), poly(E-caprolactone), poly(lactide-co-glycolide), poly(lactide-co-E-caprolactone), poly(ethylene oxide-co-E-caprolactone), poly(ethylene oxide-co-lactide), poly(ethylene oxide-colactide-co-glycolide, poly(isobutyl) cyanoacrylate, and poly(hexyl)cyanoacrylate, wherein
        (i) said poorly water soluble drug has a solubility in water of less than 5 mg/ml over the pH range of 6.5 to 7.5;
        (ii) at least 90 wt % of said drug in said nanoparticles is in a non-crystalline form; and
        (iii) said nanoparticles have an average size of less than 500 nm; and
    (b) a resuspending material selected from the group consisting of hydroxypropyl methyl cellulose acetate succinate, carboxymethyl ethylcellulose, and pharmaceutically acceptable salt forms thereof;
wherein said resuspending material constitutes from 5 wt % to 90 wt % of the combined mass of (1) said resuspending material and (2) said nanoparticles, and
wherein said composition comprises particles comprising said nanoparticles distributed throughout said resuspending material.

2. The composition of claim 1 wherein said resuspending material constitutes at least 10 wt % of said combined mass of (1) said resuspending material and (2) said nanoparticles.

3. The composition of claim 1 wherein said resuspending material constitutes at least 20 wt % of said combined mass of (1) said resuspending material and (2) said nanoparticles.

4. The composition of claim 1 wherein at least a portion of said nanoparticles are encapsulated by said resuspending material.

5. The composition of claim 1 wherein essentially all of said nanoparticles are encapsulated by said resuspending material.

6. The composition of claim 1 wherein a portion of said resuspending material is adsorbed to a surface portion of said nanoparticles.

7. The composition of claim 1 wherein said resuspending material is a salt form.

8. The composition of claim 7 wherein said salt form has a counterion selected from the group consisting of sodium, potassium, and ammonium.

9. The composition of claim 1 wherein said resuspending material is hydroxypropyl methyl cellulose acetate succinate having a methoxyl content of from 20 to 24 wt %, a hydroxypropoxyl content of from 5 to 9 wt %, an acetyl content of from 5 to 9 wt %, and a succinoyl content of from 14 to 18 wt %.

10. The composition of claim 1 wherein said poorly aqueous soluble polymer is cellulosic.

11. The composition of claim 10 wherein said poorly aqueous soluble polymer is selected from the group consisting of ethylcellulose, cellulose acetate, cellulose propionate, cellulose butyrate, and cellulose acetate butyrate.

12. The composition of claim 1 wherein the mass ratio of said drug to said poorly aqueous soluble polymer ranges from 1:9 to 2:1.

13. The composition of claim 1 wherein said nanoparticles further comprise a surface stabilizer.

14. The composition of claim 13 wherein said nanoparticles comprise from 10 to 75 wt % of said drug, from 20 to 75 wt % of said poorly aqueous soluble polymer, and from 0.1 to 40 wt % of said surface stabilizer.

15. A solid pharmaceutical composition comprising:
    (a) nanoparticles comprising a core formed of a mixture of a poorly water soluble drug and a poorly aqueous soluble polymer, wherein
        (i) said poorly water soluble drug has a solubility in water of less than 5 mg/ml over the pH range of 6.5 to 7.5;
        (ii) at least 90 wt % of said drug in said nanoparticles is in a non-crystalline form; and
        (iii) said nanoparticles have an average size of less than 500 nm; and
    (b) a resuspending material that differs from the poorly aqueous soluble polymer, the resuspending material selected from the group consisting of a pharmaceutically acceptable salt form of hydroxypropyl methyl cellulose acetate succinate and a pharmaceutically acceptable salt form of carboxymethyl ethylcellulose;
wherein said resuspending material constitutes from 5 wt % to 90 wt % of the combined mass of (1) said resuspending material and (2) said nanoparticles; and
wherein said solid pharmaceutical composition comprises particles comprising said nanoparticles distributed throughout said resuspending material wherein at least a portion of said nanoparticles are totally encapsulated by said resuspending material.

16. A process for forming a solid composition, said process comprising the steps:
    (a) forming an organic solution comprising a poorly water soluble drug and a poorly aqueous soluble polymer selected from the group consisting of ethylcellulose, propylcellulose, butylcellulose, cellulose acetate, cellulose propionate, cellulose butyrate, cellulose acetate propionate, cellulose acetate butyrate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, hydroxypropyl methylcellulose butyrate, poly(vinylacetate-co-vinyl alcohol), poly(ethylene-co-vinyl acetate), poly(ethyl acrylate-co-methylmethacrylate), poly(lactide), poly(glycolide), poly(E-caprolactone), poly(lactide-co-glycolide), poly(lactide-co-E-caprolactone), poly(ethylene oxide-co-E-caprolactone), poly(ethylene oxide-co-lactide), poly(ethylene oxide-colactide-co-glycolide, poly(isobutyl)cyanoacrylate, and poly(hexyl)cyanoacrylate, dissolved in an organic solvent, wherein said poorly water soluble drug has a solubility in water of less than 5 mg/ml over the pH range of 6.5 to 7.5;
(b) forming an aqueous solution, wherein said drug and said polymer are poorly soluble in said aqueous solution;
(c) mixing said organic solution with said aqueous solution to form a first mixture;
(d) removing said organic solvent from said first mixture to form a suspension comprising nanoparticles and said aqueous solution, wherein
  (i) said nanoparticles have an average size of less than 500 nm, and
  (ii) at least 90 wt % of the drug in said nanoparticles is non-crystalline;
(e) adding a resuspending material selected from hydroxypropyl methylcellulose acetate succinate, carboxymethyl ethylcellulose, or pharmaceutically acceptable salts thereof to either said aqueous solution of step (b) or said suspension of step (d), wherein said resuspending material constitutes from 5 wt % to 90 wt % of the combined mass of (1) said resuspending material, and (2) said nanoparticles; and
(f) removing liquid from said suspension to form a solid composition comprising particles comprising said nanoparticles distributed throughout said resuspending material.

17. The process of claim 16 wherein said liquid is removed from said suspension in step (f) by a process selected from the group consisting of spray drying, spray coating, spray layering, lyophylization, evaporation, vacuum evaporation, filtration, and combinations thereof.

18. The process of claim 16 wherein said liquid is removed from said suspension in step (f) by spray drying.

19. A solid pharmaceutical composition comprising:
(a) a plurality of nanoparticles having an average size of less than 500 nm, the nanoparticles formed of a poorly water soluble drug distributed throughout a poorly aqueous soluble polymer selected from the group consisting of ethylcellulose, propylcellulose, butylcellulose, cellulose acetate, cellulose propionate, cellulose butyrate, cellulose acetate propionate, cellulose acetate butyrate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, hydroxypropyl methylcellulose butyrate, poly(vinylacetate-co-vinyl alcohol), poly(ethylene-co-vinyl acetate), poly(ethyl acrylate-co-methylmethacrylate), poly(lactide), poly(glycolide), poly(E-caprolactone), poly(lactide-co-glycolide), poly(lactide-co-E-caprolactone), poly(ethylene oxide-co-E-caprolactone), poly(ethylene oxide-co-lactide), poly(ethylene oxide-colactide-co-glycolide, poly(isobutyl)cyanoacrylate, and poly(hexyl)cyanoacrylate, wherein
  (i) the poorly water soluble drug has a solubility in water of less than 5 mg/ml over the pH range of 6.5 to 7.5; and
  (ii) at least 90 wt % of the drug in said nanoparticles is in a non-crystalline form; and
(b) a resuspending material that is not the same material as the poorly aqueous soluble polymer, wherein the resuspending material comprises hydroxypropyl methyl cellulose acetate succinate, carboxymethyl ethylcellulose, or pharmaceutically acceptable salt forms thereof; and
wherein the resuspending material encapsulates the plurality of nanoparticles.

* * * * *